United States Patent
Baudouin et al.

(10) Patent No.: US 11,604,184 B2
(45) Date of Patent: Mar. 14, 2023

(54) JUVENILE ATOPIC DERMATITIS MODELS

(71) Applicant: Laboratoires Expanscience, Paris la Defense (FR)

(72) Inventors: Caroline Baudouin, Rambouillet (FR); Stephanie Bredif, Croisilles (FR)

(73) Assignee: Laboratoires Expanscience, Paris la Defense (FR)

( * ) Notice: Subject to any disclaimer, the term of this patent is extended or adjusted under 35 U.S.C. 154(b) by 1063 days.

(21) Appl. No.: 16/311,378

(22) PCT Filed: Jun. 23, 2017

(86) PCT No.: PCT/EP2017/065497
§ 371 (c)(1),
(2) Date: Dec. 19, 2018

(87) PCT Pub. No.: WO2017/220763
PCT Pub. Date: Dec. 28, 2017

(65) Prior Publication Data
US 2019/0234939 A1    Aug. 1, 2019

(30) Foreign Application Priority Data

Jun. 23, 2016 (FR) ..................................... 1655850

(51) Int. Cl.
| | | |
|---|---|---|
| *C12Q 1/68* | (2018.01) | |
| *G01N 33/50* | (2006.01) | |
| *C12Q 1/6883* | (2018.01) | |
| *C12N 5/00* | (2006.01) | |
| *C12N 5/071* | (2010.01) | |

(52) U.S. Cl.
CPC ....... *G01N 33/5064* (2013.01); *C12N 5/0062* (2013.01); *C12N 5/0629* (2013.01); *C12Q 1/68* (2013.01); *C12Q 1/6883* (2013.01); *G01N 33/5044* (2013.01); *C12N 2503/06* (2013.01); *C12N 2513/00* (2013.01); *C12Q 2600/106* (2013.01); *C12Q 2600/136* (2013.01); *C12Q 2600/158* (2013.01); *G01N 2500/02* (2013.01); *G01N 2500/10* (2013.01); *G01N 2800/202* (2013.01); *G01N 2800/38* (2013.01)

(58) Field of Classification Search
None
See application file for complete search history.

(56) References Cited

FOREIGN PATENT DOCUMENTS

WO    2014009566 A1    1/2014

OTHER PUBLICATIONS

Bachelor et al., "Induction of an atopic dermatitis-like phenotype in a full-thickness in vitro human skin model," Journal of Investigative Dermatology, vol. 136, No. 5, p. S62, May 2016.
Bredif et al., "In vitro models of infant skin to study molecular mechanisms involved in pediatric atopic dermatitis," Journal of Investigative Dermatology, vol. 136, No. 9, p. S222, Sep. 2016.
Bredif et al., "Studying the role of S. aureus and its biofilm in atopic dermatitis pathogenesis using invitro 3D models," Journal of Investigative Dermatology, vol. 136, No. 9, p. S220, Sep. 2016.
Castex-Rizzi et al., "In vitro approaches to pharmacological screening in the filed of atopic dermatitis," British Journal of Dermatology, vol. 170, pp. 12-18, Jul. 2014.
Ilnytska et al., "Colloidal Oatmeal (*Avena sativa*) Improves Skin Barrier Through Multi-Therapy Activity," Journal of Drugs in Dermatology, vol. 15, Issue 6, pp. 684-690, Jun. 2016.
International Search Report for International application No. PCT/EP2017/065497 dated Sep. 22, 2017.
Mathes et al., "The use of skin models in drug development," Advanced Drug Delivery Reviews, vol. 69, pp. 81-102, Dec. 2013.

*Primary Examiner* — Celine X Qian
(74) *Attorney, Agent, or Firm* — Rouget F. Henschel; Potomac Law Group, PLLC

(57) ABSTRACT

The invention relates to biomarkers in children's skin, in particular in the skin of infants, the expression of which changes when the skin is affected by atopic dermatitis. Such markers are particularly advantageous in that they allow the skin's response to atopic dermatitis to be monitored. The inventors have developed methods for evaluating the in vitro efficacy of formulations in preventing the effects of atopic dermatitis on a child's skin, using a skin model specifically capable of reproducing the characteristics of children's skin.

22 Claims, 4 Drawing Sheets

JUVENILE ATOPIC DERMATITIS MODELS

INTRODUCTION

Figure 1:
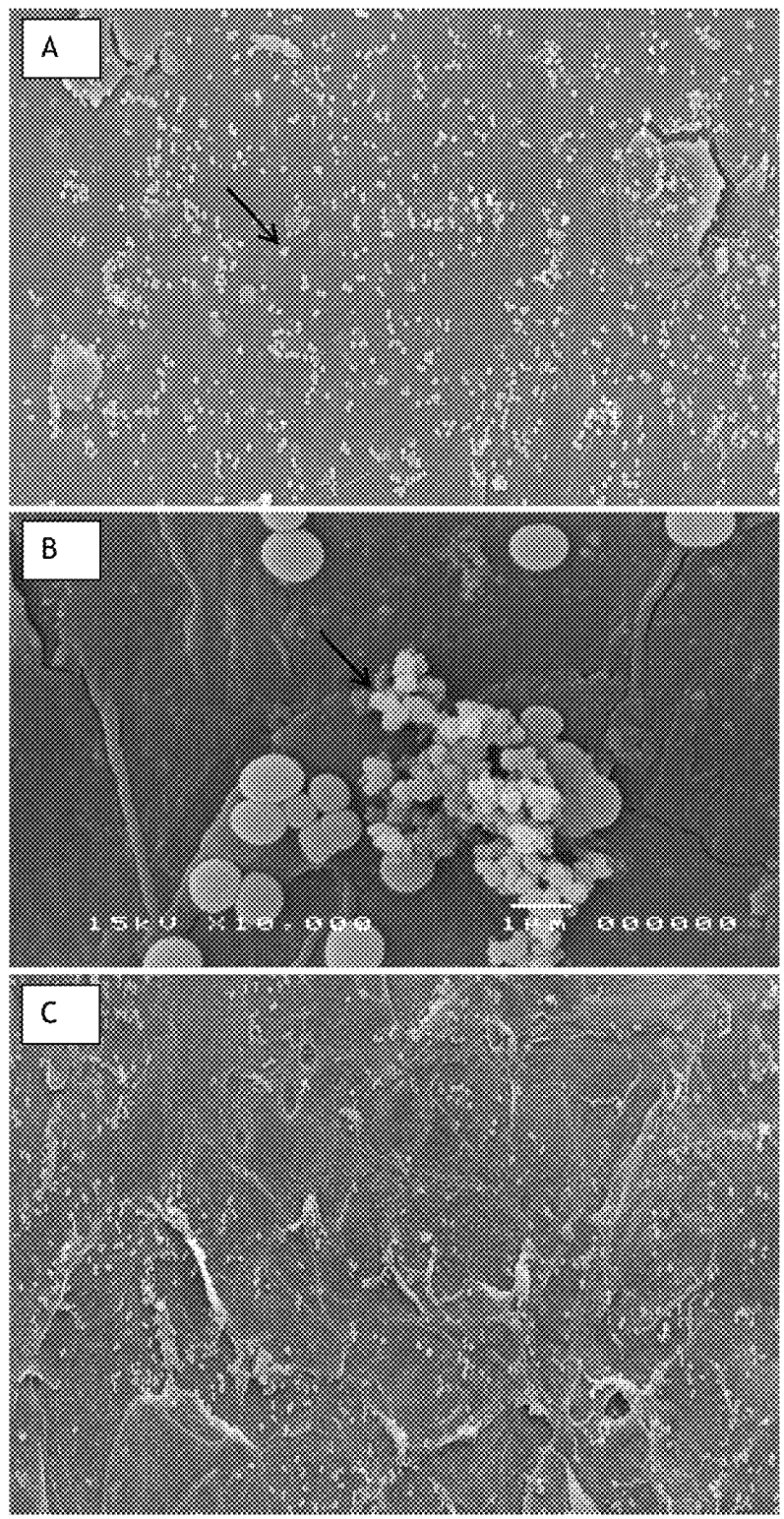

The skin is a set of cells and macromolecules grouped together in the form of a resistant and flexible tissue which covers the entire body. It is made up of two joined layers, the epidermis and the dermis, and associated subcutaneous tissues.

The main function of the skin is to establish a protective barrier against environmental insults while allowing some exchanges between the internal and external environment. The barrier function is particularly important in limiting epidermal water loss. This function is provided chiefly by the corneal layer (stratum corneum), the uppermost layer of the epidermis, composed of flattened, anucleur cells called corneocytes. The watertightness of this "brick wall" is provided by an intercellular cement composed of specific lipids (cholesterol, cholesterol sulphate, free fatty acids and ceramides). The regenerative capacity of the epidermis is conferred by adult stem cells which allow regular replacement of the differentiated cells eliminated during keratinization. This process is particularly crucial for barrier function maturation and maintenance.

Adaptation to extrauterine life is a process which begins at birth and continues throughout the first year of life. The first months of postnatal life are a period of structural and functional reorganization of the skin allowing physiological adaptation to the extrauterine environment. For example, the immaturity of newborn skin is highlighted by the difference in the structure and molecular composition of the stratum corneum compared with that of adults. These are incomplete and thus continue to develop for at least the first 12 months after birth (Chiou et al., *Skin Pharmacol Physiol*, 17: 57-66, 2004; Nikolovski et al., *J Invest Dermatol*, 128: 1728-1736, 2008; Stamatas et al., *Pediatr Dermatol*, 27: 125-131, 2010; Telofski et al., *Dermatol Res Pract*, 2012: 198789, 2012). In addition, the results of two recent clinical studies (Fluhr et al., *Br J Dermatol*, 166(3): 483-90, 2012 and Fluhr et al., *Br J Dermatol*, 2014, 171(5): 978-86) suggest that infant skin presents a certain immaturity in its ability to capture water and regulate related mechanisms. Moreover, these studies have shown that the epidermal barrier organizes structurally from birth to 2 years of age and is therefore not completely competent during this period. This helps to explain the fragility of infants' and young children's skin and its susceptibility to chemical, physical and microbial attacks.

In addition, incomplete skin maturation can have significant clinical consequences. It is therefore important to allow the skin to be constructed and to develop properly and harmoniously, otherwise its functional and structural organization could be compromised. In this respect, it is crucial to preserve the barrier function and the renewal capacity of the epidermis.

Thus, the immaturity of the barrier and of the mechanisms regulating hydration in a baby's skin contributes to make it even more vulnerable to pathological situations such as atopic dermatitis.

Atopic dermatitis is one of the most common chronic diseases in the population. It is characterized by a set of clinical signs, the most important of which are pruritus and eczematous lesions, which may be acute, subacute or chronic. It almost always begins in infants or young children, while the barrier is structurally and functionally organizing itself. Atopic dermatitis usually begins at around three months of age, but sometimes in the first few weeks of life. It progresses in alternating relapse and remission phases. Depending on the child and the severity of the condition, it may last from several months to several years. A small percentage may persist into adulthood.

Atopic dermatitis is, first and foremost, a chronic inflammatory dermatological disease combining impairment of the skin barrier and skin inflammation. In a first sensitization phase, the skin barrier defect allows allergens to penetrate through the skin. Allergens that penetrate the upper layers of the epidermis are processed (internalized) by epidermal Langerhans cells and dermal dendritic cells. Langerhans cells are antigen-presenting cells that are able to capture skin antigens, prepare them and present them to T lymphocytes. This presentation leads to activation of the Th2 response, which results in the production of inflammatory cytokines such as IL-4, IL-5 and IL-13 (see for example Bieber, Ann Dermatol. 2010, 22(2): 125-137).

Once the individual has been sensitized cutaneously, subsequent contact with the allergen in question may induce eczema lesions. This response is also mediated by the Th2 response. In particular, Langerhans cells present the peptides to specific T lymphocytes that, when activated, produce Th2 cytokines (IL-4, IL-5). The resulting cytokines will recruit new cells, including eosinophils, which play an important role in the development and chronicity of eczema lesions.

In all periods of activity of the disease, bacterial or viral skin superinfections are the most common complications. The skin of atopic dermatitis patients is highly susceptible to secondary infections, which then tend to become more widespread. For example, the bacterium *Staphylococcus aureus* is a major cause of skin infections. It commonly colonizes the skin of atopic dermatitis patients, whereas it is only transiently present on healthy skin. The bacterium then secretes virulence factors that further reduce the barrier function, exacerbating the disease and contributing to its chronicity. In addition, *S. aureus* is usually found in atopic dermatitis patients in the form of homogeneous biofilms, a form resistant to host defences and treatments.

To date, there is no cure for atopic dermatitis. Treatments are primarily local, the aim of which is to improve symptoms and control disease progression (Eichenfield et al., J Am Acad Dermatol. 2014; 70(2): 338-351; Eichenfield et al., J Am Acad Dermatol. 2014; 71(1): 116-132). In particular, the daily use of emollients is essential to restore and protect the damaged skin barrier. Many different emollients are available on the market. However, the precise mechanisms by which they exert their beneficial effects are insufficiently understood. Yet, atopic dermatitis has many aspects. A priori, there is no reason to believe that an emollient will be able to restore the barrier in each of its particular pathological situations. In this respect, it is important to note that experimental data for selecting specific preparations are rare. In fact, there are very few comparative studies of their relative efficacy.

There thus remains a need for appropriate tests for selecting effective, well-tolerated emollients to treat all aspects of atopic dermatitis.

DESCRIPTION

Atopic dermatitis is a condition that affects mainly children and, in particular, infants. It is principally characterized by an interaction between a barrier defect and an inflammatory reaction. It manifests itself in many and varied aspects that are generally not taken into account when developing new active agents or new emollients. The pathophysiology of atopic dermatitis is complex and involves multiple parameters (barrier function, immune response, inflammation, microbiota, etc.); it is difficult to reproduce all these factors simultaneously in vitro. Indeed, existing in vitro models of atopic dermatitis are limited by the fact that they do not correspond to the overall picture of the disease but represent only some of the factors involved in the pathogenesis.

The inventors have developed processes for evaluating the in vitro efficacy of cosmetic active agents, emollients and formulations on the prevention and treatment of all aspects of atopic dermatitis affecting children's skin. Such processes had never been described until now. Reconstructed skins specifically capable of reproducing the characteristics of children's skin, and in particular that of very young children such as infants, have been used to reproduce all phases of atopic dermatitis. The use of this variety of models, corresponding to the different phases of the pathology, makes it possible to select the tested cosmetic active agents, emollients and formulations that are genuinely effective against atopic dermatitis. The cosmetic active agents, emollients and formulations thus selected are particularly effective on all major parameters of atopic dermatitis pathophysiology (barrier function, immunity, inflammation, microbiota). The invention thus makes it possible to determine precisely which cosmetic active agents and which emollients have a beneficial effect on the prevention or treatment of the effects of atopic dermatitis. The methods of the invention are also suitable for evaluating the activity of formulations. The inventors were thus able to show that certain formulations were more effective than others in preventing and/or limiting the effects of atopic dermatitis, thus demonstrating the usefulness of the approach.

The invention thus relates to a method for evaluating the efficacy of a cosmetic active agent, an emollient or a formulation in treating and/or preventing atopic dermatitis, comprising evaluating the efficacy of said active agent, emollient or formulation in several models each reproducing a specific phase or a characteristic of atopic dermatitis pathophysiology.

"Atopic skin", as used herein, refers to an atopic dermatitis patient's skin or to skin with the same physiological and molecular characteristics as an atopic dermatitis patient's skin. "Atopic dermatitis" (or constitutional eczema), as used herein, refers to a chronic pruritic inflammatory condition common in children and young adults, and characterized in particular by a predominant epidermal insult with an influx of T lymphocytes (exocytosis) and intercellular oedema (spongiosis) producing microscopic vesicles. Atopic dermatitis is the skin manifestation of atopy, characterized by the existence of hypersensitivity manifestations mediated by IgE and specific T lymphocytes.

Atopic dermatitis is caused by a weakening of the skin barrier that allows a Th2-cytokine-mediated inflammatory reaction. The term "cytokine", as used herein, refers to a family of small secreted regulatory proteins that play a crucial role in immune responses. Cytokines are involved in communication between cells and regulate many cellular functions, such as cell survival and growth, as well as induction of expression of many genes. "Th2 cytokines", as used herein, means the cytokines produced by Th2 CD4 T lymphocytes (IL-4, IL-5, IL-10, IL-13, IL-22 and IL-31) or produced by other cell types in the same context signalling Th2 pathway activation (TSLP and TNFα). Cytokines can be produced by many cell types, especially resident mononuclear phagocytes (macrophages and dendritic cells) and mast cells. For a review of Th2 cytokines and their role in atopic dermatitis, refer for example to Brandt and Sivaprasad (*J Clin Cell Immunol.* 2011; 2(3): 110).

The present inventors have developed models for studying the different phases of the disease and thus for selecting cosmetic active agents or emollients capable of restoring the skin barrier and modulating the inflammatory processes involved in the pathology in each of these phases. For example, the inventors developed models of reconstructed skin from samples taken from children and were able to test the effect of atopic dermatitis on these models. While atopic dermatitis in the models of the prior art was particularly related to the absence of filaggrin (Mildner et al., *J Invest Dermatol.* 2010; 130(9): 2286-2294; Pendaries et al., *J Invest Dermatol.* 2014; 134(12): 2938-2946), the present inventors used several different conditions to reproduce in vitro the different stages of the disease and characterize them molecularly.

First, the reconstructed skin models used were obtained from skin samples from children. Unlike adult skin, children's skin is not mature, while the structural and functional organization of the barrier is not completely competent. However, atopic dermatitis chiefly affects children. On the other hand, the initiation phase of atopic dermatitis has been reproduced by adding to reconstructed children's epidermises stimulated by a mixture of poly (I:C) and cytokine IL1α (the protein sequence of human interleukin IL1α is represented by the reference sequence NCBI: NP_000566, and is encoded by the human IL1A gene (NCBI reference: Gene ID: 3552), whose sequence corresponds to the reference NCBI: NM_000575). The stress induced by this mixture of molecules leads to induction of a Th2 inflammatory response typical of initiation of an inflammatory response characteristic of atopic dermatitis. In addition, the inflammatory response established was reproduced in another model by adding a cocktail of Th2 cytokines to reconstructed children's epidermises. Indeed, when at least two cytokines selected from the group consisting of IL-4, IL-5, IL-10, IL-13, IL-22, IL-31, TSLP1 and TNFα, and preferentially when a cocktail consisting of IL-4, IL-13, IL-22 and TNFα, are brought into contact with reconstructed children's skin, the model obtained has the same physiological characteristics as atopic skins in vivo. In particular, this model has specific marker expression profiles similar to those of atopic skin.

Finally, two other models were developed to mimic the complications of atopic dermatitis, notably bacterial infections.

"Bacterial infection", as used herein, refers to the establishment, proliferation and maintenance of pathogenic bacteria on the surface of the skin, notably on atopic skin.

A "pathogenic bacterium" in the context of the present application is a bacterium that can cause disease in a host, more preferentially a skin disease. A pathogenic bacterium may be an opportunistic pathogenic bacterium or a strict pathogenic bacterium. An "opportunistic pathogenic bacterium" is a bacterium that does not usually cause disease in healthy subjects, but which may become pathogenic in subjects with weakened defences. These bacteria are often commensal bacteria living on the surface of human skin and mucous membranes. A "strict pathogenic bacterium" is a bacterium that is pathogenic regardless of the host. The pathogenic bacteria responsible for the most common skin infections are staphylococci such as *Staphylococcus aureus* and *Staphylococcus epidermidis*, streptococci, notably *Streptococcus pyagenes* and *Streptococcus agalactiae*, corynebacteria and propionic bacteria. Preferentially, a pathogenic bacterium according to the invention is a *staphylococcus* or a *streptococcus*; more preferentially, a pathogenic bacterium according to the invention is selected from

*S. aureus* and *S. pyagenes*; even more preferentially, the pathogenic bacterium according to the invention is *S. aureus*.

In the first model of bacterial infection of children's atopic skin, the reconstituted skin model is cultured in the presence of THP-1 monocytes. This human monocytic cell line, which is available from the American Type Culture Collection (ATCC, 10801 University Boulevard, Manassas, Va. 20110 USA), is well known to the skilled person for its ability to differentiate into macrophages and to synthesize cytokines. The reconstructed skin model of the invention cultured in the presence of THP-1 monocytes therefore represents a particularly realistic immune-mediated response model, which makes it possible to study infection by a pathogenic bacterium under conditions very similar to those existing in vivo. The second model makes it possible to monitor the evolution of a population of pathogenic bacteria when colonization of atopic skin is already established.

The inventors were able to observe that the expression of certain biological markers was impaired when these models of reconstructed children's skin were cultured under various atopic dermatitis conditions. Certain markers, such as markers of inflammation, were more strongly expressed, while the expression of others, such as stem cell markers or those strengthening the barrier function, was decreased. On the other hand, variations in expression of these markers were reduced, or even eliminated, when the models were treated with cosmetic active agents, emollients or formulations known to treat or prevent atopic dermatitis. This result underlines the physiological relevance of these markers. The importance of using reconstructed skin models of children and not of adults to isolate such markers is further reinforced.

Thus, the present inventors were able to identify biological markers whose expression is modified by atopic dermatitis in children's skin. Such markers are particularly advantageous because they make it possible to monitor the skin's response during the development of the disease.

According to a first aspect, the invention relates to a method for evaluating the in vitro efficacy of a cosmetic active agent, an emollient or a formulation in preventing or treating the effects of atopic dermatitis affecting children's skin, said method comprising determining the expression and/or activation level of at least one biological marker.

More precisely, the invention relates to a method for evaluating the in vitro efficacy of a cosmetic active agent, an emollient or a formulation in preventing or treating the effects of atopic dermatitis affecting children's skin, said method comprising determining the efficacy of said cosmetic active agent, emollient or formulation in each of the four tests A, B, C and D, said method being characterized in that:

test A comprises the following steps:
a) obtaining a reconstructed skin model from a skin sample from a child;
b) contacting said cosmetic active agent, emollient or formulation with the reconstructed skin model of step a);
c) contacting the reconstructed skin model of step b) with a solution comprising poly(deoxyinosinic-deoxycytidylic) acid (poly(dIdC)) and interleukin 1 alpha (IL1α);
d) measuring the expression level of at least one biological marker in the skin model of step c); and
e) evaluating the efficacy of said cosmetic active agent, emollient or formulation based on the level of step d);

test B comprises the following steps:
a) obtaining a reconstructed skin model from a skin sample from a child;
b) contacting said cosmetic active agent, emollient or formulation with the reconstructed skin model of step a);
c) contacting the reconstructed skin model of step b) with a solution comprising at least two Th2 cytokines;
d) measuring the expression level of at least one biological marker in the skin model of step c); and
e) evaluating the efficacy of said cosmetic active agent, emollient or formulation based on the level of step d);

test C comprises the following steps:
a) obtaining a reconstructed skin model from a skin sample from a child;
b) growing the reconstructed skin model of step a) in the presence of THP-1 monocytes;
c) contacting said cosmetic active agent, emollient or formulation with the reconstructed skin model of step b);
d) inducing an impairment of the barrier function in the reconstructed skin model of step c);
e) contacting the reconstructed skin model of step d) with at least one pathogenic bacterium;
f) measuring the expression and/or activation level of at least one biological marker in the skin model of step e); and
g) evaluating the efficacy of said cosmetic active agent, emollient or formulation based on the level of step f); and test D comprises the following steps:
a) obtaining a reconstructed skin model from a skin sample from a child;
b) contacting said cosmetic active agent, emollient or formulation with the reconstructed skin model of step a);
c) inducing an impairment of the barrier function in the reconstructed skin model of step b);
d) contacting the reconstructed skin model of step c) with at least one pathogenic bacterium;
e) measuring the expression and/or activation level of at least one biological marker in the skin model of step d); and
f) evaluating the efficacy of said cosmetic active agent, emollient or formulation based on the level of step e).

The expression "impairment of the barrier function", as used herein, refers to an impairment of the integrity of the barrier function. The barrier function of the skin or skin barrier (as used herein, the two terms are synonymous) is integrated when the skin barrier is fully functional, meaning that exchanges, and notably the diffusion of water, are limited. On the other hand, an impairment of the barrier function is an impairment leading to a reduction of the barrier function of the reconstructed skin model used and therefore to an increase in exchanges, and notably the diffusion of water.

The integrity of the skin barrier can be assessed by measuring a large number of parameters. In particular, it is common to determine the integrity of the skin barrier by measuring insensible water loss, also called transepidermal water loss. The methods for measuring insensible water loss are well known to the skilled person and do not need to be described in detail here (see for example H Tagami and K Kikuchi. "Diseases that affect barrier function". In Elias P M and Feingold K R editors. Skin Barrier. New York: Taylor and Francis; 2005. p. 447-468). Preferentially, an evaporimeter, which consists of a probe placed 3 or 6 mm above the skin, is used to measure insensible water loss.

Barrier integrity can be affected by a large number of factors well known to the skilled person. An impairment of the skin barrier may occur as a result of external insults such as irritants (detergents, acids, bases, oxidants, reducers, concentrated solvents, toxic gases or fumes), mechanical stresses (friction, impact, abrasion, surface tearing, projection of dust or particles, shaving or depilation), thermal or climatic imbalances (cold, dryness), xenobiotics (undesirable microorganisms, allergens) or internal insults resulting from psychological stress or more generally during skin ageing. For example, an inactivating mutation in the filaggrin gene leads to reduced barrier function and is a major cause of atopic dermatitis (see for example, Peng Et Novak, *Clinical & Experimental Allergy,* 2015, 45: 566-574; Weidinger Et Novak, *Lancet.* 2016, 387: 1109-1122). Preferably, the skin barrier impairment results from mechanical stress, such as, for example, slight abrasion of the surface of the reconstituted skin.

In a first preferred embodiment, the reconstructed skin model is contacted (brought into contact) with the poly (dIdC) and ILa solution in step c) of test A in the presence of the cosmetic active agent, the emollient or the formulation. According to another preferred embodiment, the cosmetic active agent, the emollient or the formulation is removed prior to exposure of said reconstructed skin model to said solution during said step c).

According to another preferred embodiment, the reconstructed skin model is contacted with the at least two Th2 cytokines in step c) of test B in the presence of the cosmetic active agent, the emollient or the formulation. According to another preferred embodiment, the cosmetic active agent, the emollient or the formulation is removed prior to exposure of said reconstructed skin model to the at least two Th2 cytokines during said step c).

According to yet another preferred embodiment, the reconstructed skin model is contacted (brought into contact) with at least one pathogenic bacterium in step e) of test C in the presence of the cosmetic active agent, the emollient or the formulation. According to another preferred embodiment, the cosmetic active agent, the emollient or the formulation is removed prior to exposure of said reconstructed skin model to at least one pathogenic bacterium during said step e).

According to yet another preferred embodiment, the reconstructed skin model is brought into contact with at least one pathogenic bacterium in step d) of test D in the presence of the cosmetic active agent, the emollient or the formulation. According to another preferred embodiment, the cosmetic active agent, the emollient or the formulation is removed prior to exposure of said reconstructed skin model to at least one pathogenic bacterium during said step d).

The skilled person will easily understand that these different embodiments may be combined as needed. However, it is more advantageous to follow the same approach in each of the four tests. For example, if the reconstructed skin model is brought into contact with the poly(dldC) and ILa solution in step c) of test A in the presence of the cosmetic active agent, the emollient or the formulation, it is preferable that the reconstructed skin model is brought into contact with the at least two Th2 cytokines in step c) of test B in the presence of the cosmetic active agent, the emollient or the formulation and that the reconstructed skin model is brought into contact with at least one pathogenic bacterium in step e) of test C in the presence of the cosmetic active agent, the emollient or the formulation and that the reconstructed skin model is brought into contact with at least one pathogenic bacterium in step d) of test D in the presence of the cosmetic active agent, the emollient or the formulation. On the other hand, if the cosmetic active agent, the emollient or the formulation is removed prior to exposure of said reconstructed skin model to said solution during step c) of test A, then it is preferable that the cosmetic active agent, the emollient or the formulation is removed prior to exposure of said reconstructed skin model to the at least two Th2 cytokines during step c) of test B and that the cosmetic active agent, the emollient or the formulation is removed prior to exposure of said reconstructed skin model to at least one pathogenic bacterium during step e) of test C and that the cosmetic active agent, the emollient or the formulation is removed prior to exposure of said reconstructed skin model to at least one pathogenic bacterium during step d) of test D.

According to a preferred embodiment, the reconstructed skin model may be brought into contact with the poly(dIdC) and ILa solution before being exposed to the cosmetic active agent, the emollient or the formulation in test A. According to another preferred embodiment, the reconstructed skin model may be brought into contact with the at least two Th2 cytokines before being exposed to the cosmetic active agent, the emollient or the formulation in test B. According to yet another preferred embodiment, the reconstructed skin model may be brought into contact with at least one pathogenic bacterium before being exposed to the cosmetic active agent, the emollient or the formulation in test C. According to yet another preferred embodiment, the reconstructed skin model may be brought into contact with at least one pathogenic bacterium before being exposed to the cosmetic active agent, the emollient or the formulation in test D. Such embodiments may be particularly advantageous for studying the effects of said cosmetic active agent, emollient or formulation in the treatment of atopic dermatitis.

In addition, the invention also relates to a method for evaluating the in vitro efficacy of a cosmetic active agent, an emollient or a formulation in preventing or reducing the effects of atopic dermatitis of children's skin.

Said method comprises determining the efficacy of said cosmetic active agent, emollient or formulation in each of the four tests A, B, C and D, said method being characterized in that:

test A comprises the following steps:
a) obtaining a reconstructed skin model from a skin sample from a child;
b) contacting the reconstructed skin model of step a with a solution comprising poly(deoxyinosinic-deoxycytidylic) acid (poly(dIdC)) and interleukin 1 alpha (IL1α);
c) contacting said cosmetic active agent, emollient or formulation with the reconstructed skin model of step b);
d) measuring the expression level of at least one biological marker in the skin model of step c); and
e) evaluating the efficacy of said cosmetic active agent, emollient or formulation based on the level of step d);

test B comprises the following steps:
a) obtaining a reconstructed skin model from a skin sample from a child;
b) contacting the reconstructed skin model of step a) with a solution comprising at least two Th2 cytokines;
c) contacting said cosmetic active agent, emollient or formulation with the reconstructed skin model of step b);
d) measuring the expression level of at least one biological marker in the skin model of step c); and
e) evaluating the efficacy of said cosmetic active agent, emollient or formulation based on the level of step d);

test C comprises the following steps:
a) obtaining a reconstructed skin model from a skin sample from a child;
b) growing the reconstructed skin model of step a) in the presence of THP-1 monocytes;
c) inducing an impairment of the barrier function in the reconstructed skin model of step b);
d) contacting the reconstructed skin model of step c) with at least one pathogenic bacterium;
e) contacting said cosmetic active agent, emollient or formulation with the reconstructed skin model of step d);
f) measuring the expression and/or activation level of at least one biological marker in the skin model of step e); and
g) evaluating the efficacy of said cosmetic active agent, emollient or formulation based on the level of step f); and test D comprises the following steps:
a) obtaining a reconstructed skin model from a skin sample from a child;
b) inducing an impairment of the barrier function in the reconstructed skin model of step a);
c) contacting the reconstructed skin model of step b) with at least one pathogenic bacterium;
d) contacting said cosmetic active agent, emollient or formulation with the reconstructed skin model of step c);
e) measuring the expression and/or activation level of at least one biological marker in the skin model of step d); and
f) evaluating the efficacy of said cosmetic active agent, emollient or formulation based on the level of step e).

The skilled person will easily understand that steps b) and c) of test A may be performed simultaneously or successively, according to need. In other words, the reconstructed skin model may be cultured in step b) in the presence of the poly(dIdC) and ILa solution and, in addition, in the presence of the cosmetic active agent, the emollient or the formulation. Alternatively, the skin model may first be cultured under conditions where it is exposed to the poly(dIdC) and ILa solution, then brought into contact with the cosmetic active agent, the emollient or the formulation.

Similarly, steps b) and c) of test B may be performed simultaneously or successively, according to the skilled person's needs. In other words, the reconstructed skin model may be cultured in step b) in the presence of at least two Th2 cytokines and, in addition, in the presence of the cosmetic active agent, the emollient or the formulation. Alternatively, the skin model may first be cultured under conditions where it is exposed to at least two Th2 cytokines, then brought into contact with the cosmetic active agent, the emollient or the formulation.

Also similarly, steps c), d) and e) of test C may be performed simultaneously or successively, according to the skilled person's needs. In other words, the reconstructed skin model may be exposed in step c) to conditions where the barrier function is impaired in the presence of at least one pathogenic bacterium and, in addition, in the presence of the cosmetic active agent, the emollient or the formulation. Alternatively, the skin model may first be exposed to conditions where it undergoes an impairment of its barrier function, before being exposed to at least one pathogenic bacterium, to finally be brought into contact with the cosmetic active agent, the emollient or the formulation.

Still similarly, steps b), c) and d) of test D may be performed simultaneously or successively, according to the skilled person's needs. In other words, the reconstructed skin model may be cultured in step b) under conditions where the barrier function is impaired and in the presence of at least one pathogenic bacterium and, in addition, in the presence of the cosmetic active agent, the emollient or the formulation. Alternatively, the skin model may first be cultured under conditions where it undergoes an impairment of its barrier function, before being exposed to at least one pathogenic bacterium, to finally be brought into contact with the cosmetic active agent, the emollient or the formulation.

The skilled person will easily understand that these different embodiments may be combined as needed. However, it is more advantageous to follow the same approach in each of the four tests. For example, if steps b) and c) of test A are performed simultaneously, it is preferable that steps b) and c) of test B are also performed simultaneously and that steps c), d) and e) of test C are also performed simultaneously and that steps b), c) and d) of test D are also performed simultaneously. On the other hand, if steps b) and c) of test A are performed successively, it is preferable that steps b) and c) of test B are also performed successively and that steps c), d) and e) of test C are also performed successively and that steps b), c) and d) of test D are also performed successively.

The expression "the efficacy of a cosmetic active agent, an emollient or a formulation in preventing or reducing the effects of atopic dermatitis" means, for the purposes of the present application, the ability of the cosmetic active agent, the emollient or the formulation to abolish or reduce said effects of atopic dermatitis. In the present case, prevention refers to treatment administered before the effects of the condition develop, while reduction refers to treatment administered after the effects of atopic dermatitis have appeared.

"Child", according to the invention, means an individual whose age is less than or equal to 16 years. Thus, the category of children according to invention includes newborns aged between 0 and 1 month, infants aged between 1 month and 2 years, and children themselves, aged at least 2 years. A "newborn", as meant herein, may be a full-term or premature birth.

To avoid any ambiguity, the term "child" used in the present application without further clarification should be understood in its most general sense, i.e. as referring to a person aged 16 or under. An "adult" for the purposes of the present invention is a person who is not a child, i.e. a person over the age of 16.

According to a preferred embodiment, the sample donor is more particularly a donor aged between 0 and 1 month, between 1 month and 2 years or between 2 and 16 years. In other words, according to this embodiment, the sample donor is selected from the group consisting of newborns aged between 0 and 1 month, infants aged between 1 month and 2 years, and children aged between 2 years and 16 years. More preferentially, the sample donor is a newborn or an infant.

Preferably, the method of the invention may be used regardless of the ethnic or geographical origin of the skin, or the phototype thereof. It may thus be of Caucasian, African, Asian, South American, Melanesian or other origin; it may also have a phototype I, II, III, IV, V or VI, without this affecting the invention. Indeed, the purpose of the method of the invention is to identify biological markers characterizing any type of skin and depending only on the donor's age.

It is important to verify that the cosmetic active agents, emollients and formulations of the invention are well tolerated. For example, certain products currently on the market may cause irritation if used regularly. Such an effect may only worsen developing or existing skin inflammation caused by atopic dermatitis.

According to another aspect, the invention thus relates to a method for evaluating the tolerance of a cosmetic active agent, an emollient or a formulation by children's atopic skin, said method comprising determining the tolerance of said cosmetic active agent, emollient or formulation by said children's atopic skin in each of the four tests A, B, C and D, said method being characterized in that:

test A comprises the following steps:
a) obtaining a reconstructed skin model from a skin sample from a child;
b) contacting said cosmetic active agent, emollient or formulation with the reconstructed skin model of step a);
c) contacting the reconstructed skin model of step b) with a solution comprising poly(deoxyinosinic-deoxycytidylic) acid and interleukin 1 alpha (IL1α);
d) measuring the expression level of at least one biological marker in the skin model of step c); and
e) determining whether said cosmetic active agent, emollient or formulation is well tolerated by children's atopic skin based on the level of step d);

test B comprises the following steps:
a) obtaining a reconstructed skin model from a skin sample from a child;
b) contacting said cosmetic active agent, emollient or formulation with the reconstructed skin model of step a);
c) contacting the reconstructed skin model of step b) with a solution comprising at least two Th2 cytokines;
d) measuring the expression level of at least one biological marker in the skin model of step c); and
e) determining whether said cosmetic active agent, emollient or formulation is well tolerated by children's atopic skin based on the level of step d);

test C comprises the following steps:
a) obtaining a reconstructed skin model from a skin sample from a child;
b) growing the reconstructed skin model of step a) in the presence of THP-1 monocytes;
c) contacting said cosmetic active agent, emollient or formulation with the reconstructed skin model of step b);
d) inducing an impairment of the barrier function in the reconstructed skin model of step c);
e) contacting the reconstructed skin model of step d) with at least one pathogenic bacterium;
f) measuring the expression and/or activation level of at least one biological marker in the skin model of step e); and
g) determining whether said cosmetic active agent, emollient or formulation is well tolerated by children's atopic skin based on the level of step f); and test D comprises the following steps:
a) obtaining a reconstructed skin model from a skin sample from a child;
b) contacting said cosmetic active agent, emollient or formulation with the reconstructed skin model of step a);
c) inducing an impairment of the barrier function in the reconstructed skin model of step b);
d) contacting the reconstructed skin model of step c) with at least one pathogenic bacterium;

e) measuring the expression and/or activation level of at least one biological marker in the skin model of step d); and
f) determining whether said cosmetic active agent, emollient or formulation is well tolerated by children's atopic skin based on the level of step e).

The method of the invention may further include a comparison of cell viability in the reconstructed skin model treated with the cosmetic active agent, the emollient or the formulation and in the control reconstructed skin model, i.e. children's skin in which atopic dermatitis has been generated in at least one of the four tests above, but which has not been treated with the cosmetic active agent, the emollient or the formulation. In this case, the cosmetic active agent, the emollient or the cosmetic formulation is well tolerated by children's skin if the cell viability of the reconstructed skin model is not affected by the presence of the cosmetic active agent, the emollient or the formulation.

According to another preferred embodiment, the method of the invention thus comprises an additional step of determining the cell viability in the model of reconstructed children's atopic skin treated with the cosmetic active agent, the emollient or the cosmetic formulation, determining the cell viability of the control reconstructed skin model and comparing the two. This additional step may be performed for at least one of the tests A, B, C and D above; preferably, it is performed for each of these tests.

Many tests for determining cell viability are available to the skilled person and are commonly used in cosmetics science. Particular mention may be made of the MTT test, described for example in Mosman et al. (*J Immunol Methods*, 65(1-2): 55-63, 1983).

In to another aspect, the invention makes it possible to isolate cosmetic active agents, emollients or formulations having an effect in preventing the effects of atopic dermatitis on children's skin. As the experimental examples show, the invention makes it possible in particular to distinguish cosmetic active agents, emollients or formulations according to their activity in preventing the effects of atopic dermatitis affecting children's skin. The invention is therefore particularly suitable for identifying cosmetic active agents, emollients or formulations appropriate for this very specific skin.

The invention thus also relates to a method for identifying a cosmetic active agent, an emollient or a formulation for preventing the effects of atopic dermatitis of children's skin, said method comprising determining the efficacy of said cosmetic active agent, emollient or formulation in preventing the effects of atopic dermatitis of children's skin in each of the four tests A, B, C and D, said method being characterized in that:

test A comprises the following steps:
a) obtaining a reconstructed skin model from a skin sample from a child;
b) contacting said cosmetic active agent, emollient or with the reconstructed skin model of step a);
c) contacting the reconstructed skin model of step b) with a solution comprising poly(deoxyinosinic-deoxycytidylic) acid and interleukin 1 alpha (IL1α);
d) measuring the expression level of at least one biological marker in the skin model of step c); and
e) determining whether said candidate cosmetic active agent, emollient or formulation is a cosmetic active agent, emollient or formulation for preventing the effects of atopic dermatitis on children's skin based on the level in step d);

test B comprises the following steps:

a) obtaining a reconstructed skin model from a skin sample from a child;
b) contacting said cosmetic active agent, emollient or formulation the reconstructed skin model of step a);
c) contacting the reconstructed skin model of step b) with a solution comprising at least two Th2 cytokines;
d) measuring the expression level of at least one biological marker in the skin model of step c); and
e) determining whether said candidate cosmetic active agent, emollient or formulation is a cosmetic active agent, emollient or formulation for preventing the effects of atopic dermatitis on children's skin based on the level in step d);

test C comprises the following steps:
a) obtaining a reconstructed skin model from a skin sample from a child;
b) growing the reconstructed skin model of step a) in the presence of THP-1 monocytes;
c) contacting said cosmetic active agent, emollient or formulation with the reconstructed skin model of step b);
d) inducing an impairment of the barrier function in the reconstructed skin model of step c);
e) contacting the reconstructed skin model of step d) with at least one pathogenic bacterium;
f) measuring the expression and/or activation level of at least one biological marker in the skin model of step e); and
g) determining whether said candidate cosmetic active agent, emollient or formulation is a cosmetic active agent, emollient or formulation for preventing the effects of atopic dermatitis on children's skin based on the level of step f); and test D comprises the following steps:
a) obtaining a reconstructed skin model from a skin sample from a child;
b) contacting said cosmetic active agent, emollient or formulation into contact with the reconstructed skin model of step a);
c) inducing an impairment of the barrier function in the reconstructed skin model of step b);
d) contacting the reconstructed skin model of step c) with at least one pathogenic bacterium;
e) measuring the expression and/or activation level of at least one biological marker in the skin model of step d); and
f) determining whether said candidate cosmetic active agent, emollient or formulation is a cosmetic active agent, emollient or formulation for preventing the effects of atopic dermatitis on children's skin based on the level in step e).

In a first preferred embodiment, the reconstructed skin model is brought into contact with the poly(dldC) and ILa solution in step c) of test A in the presence of the cosmetic active agent, the emollient or the formulation. According to another preferred embodiment, the cosmetic active agent, the emollient or the formulation is removed prior to exposure of said reconstructed skin model to said solution during said step c).

According to another preferred embodiment, the reconstructed skin model is brought into contact with the at least two Th2 cytokines in step c) of test B in the presence of the cosmetic active agent, the emollient or the formulation. According to another preferred embodiment, the cosmetic active agent, the emollient or the formulation is removed prior to exposure of said reconstructed skin model to the at least two Th2 cytokines during said step c).

According to yet another preferred embodiment, the reconstructed skin model is brought into contact with at least one pathogenic bacterium in step e) of test C in the presence of the cosmetic active agent, the emollient or the formulation. According to another preferred embodiment, the cosmetic active agent, the emollient or the formulation is removed prior to exposure of said reconstructed skin model to at least one pathogenic bacterium during said step e).

According to yet another preferred embodiment, the reconstructed skin model is brought into contact with at least one pathogenic bacterium in step d) of test D in the presence of the cosmetic active agent, the emollient or the formulation. According to another preferred embodiment, the cosmetic active agent, the emollient or the formulation is removed prior to exposure of said reconstructed skin model to at least one pathogenic bacterium during said step d).

The skilled person will easily understand that these different embodiments may be combined as needed. However, it is more advantageous to follow the same approach in each of the four tests. For example, if the reconstructed skin model is brought into contact with the poly(dldC) and ILa solution in step c) of test A in the presence of the cosmetic active agent, the emollient or the formulation, it is preferable that the reconstructed skin model is brought into contact with the at least two Th2 cytokines in step c) of test B in the presence of the cosmetic active agent, the emollient or the formulation and that the reconstructed skin model is brought into contact with at least one pathogenic bacterium in step e) of test C in the presence of the cosmetic active agent, the emollient or the formulation and that the reconstructed skin model is brought into contact with at least one pathogenic bacterium in step d) of test D in the presence of the cosmetic active agent, the emollient or the formulation. On the other hand, if the cosmetic active agent, the emollient or the formulation is removed prior to exposure of said reconstructed skin model to said solution during step c) of test A, then it is preferable that the cosmetic active agent, the emollient or the formulation is removed prior to exposure of said reconstructed skin model to the at least two Th2 cytokines during step c) of test B and that the cosmetic active agent, the emollient or the formulation is removed prior to exposure of said reconstructed skin model to at least one pathogenic bacterium during step e) of test C and that the cosmetic active agent, the emollient or the formulation is removed prior to exposure of said reconstructed skin model to at least one pathogenic bacterium during step d) of test D.

According to a preferred embodiment, the reconstructed skin model may be brought into contact with the poly(dldC) and ILa solution before being exposed to the cosmetic active agent, the emollient or the formulation in test A. According to another preferred embodiment, the reconstructed skin model may be brought into contact with the at least two Th2 cytokines before being exposed to the cosmetic active agent, the emollient or the formulation in test B. According to yet another preferred embodiment, the reconstructed skin model may be brought into contact with at least one pathogenic bacterium before being exposed to the cosmetic active agent, the emollient or the formulation in test C. According to yet another preferred embodiment, the reconstructed skin model may be brought into contact with at least one pathogenic bacterium before being exposed to the cosmetic active agent, the emollient or the formulation in test D. Such embodiments may be particularly advantageous for studying the effects of said cosmetic active agent, emollient or formulation in the treatment of atopic dermatitis.

In addition, the method of the invention makes it possible to isolate cosmetic active agents, emollients or formulations for reducing the effects of atopic dermatitis affecting children's skin, said method comprising determining the efficacy of said cosmetic active agent, emollient or formulation in reducing the effects of atopic dermatitis of children's skin in each of the four tests A, B, C and D, said method being characterized in that:

test A comprises the following steps:
a) obtaining a reconstructed skin model from a skin sample from a child;
b) contacting the reconstructed skin model of step a) with a solution comprising poly(deoxyinosinic-deoxycytidylic) acid and interleukin 1 alpha (IL1α);
c) contacting said cosmetic active agent, emollient or formulation with the reconstructed skin model of step b);
d) measuring the expression level of at least one biological marker in the skin model of step c); and
e) determining whether said candidate cosmetic active agent, emollient or formulation is a cosmetic active agent, emollient or formulation for reducing the effects of atopic dermatitis on children's skin based on the level of step d);

test B comprises the following steps:
a) obtaining a reconstructed skin model from a skin sample from a child;
b) contacting the reconstructed skin model of step a) with a solution comprising at least two Th2 cytokines;
c) contacting said cosmetic active agent, emollient or formulation with the reconstructed skin model of step b);
d) measuring the expression level of at least one biological marker in the skin model of step c); and
e) determining whether said candidate cosmetic active agent, emollient or formulation is a cosmetic active agent, emollient or formulation for reducing the effects of atopic dermatitis on children's skin based on the level of step d);

test C comprises the following steps:
a) obtaining a reconstructed skin model from a skin sample from a child;
b) growing the reconstructed skin model of step a) in the presence of THP-1 monocytes;
c) inducing an impairment of the barrier function in the reconstructed skin model of step b);
d) contacting the reconstructed skin model of step c) with at least one pathogenic bacterium;
e) contacting said cosmetic active agent, emollient or formulation with the reconstructed skin model of step d);
f) measuring the expression and/or activation level of at least one biological marker in the skin model of step e); and
g) determining whether said candidate cosmetic active agent, emollient or formulation is a cosmetic active agent, emollient or formulation for reducing the effects of atopic dermatitis on children's skin based on the level of step f); and test D comprises the following steps:
a) obtaining a reconstructed skin model from a skin sample from a child;
b) inducing an impairment of the barrier function in the reconstructed skin model of step a);
c) contacting the reconstructed skin model of step b) with at least one pathogenic bacterium;
d) contacting said cosmetic active agent, emollient or formulation with the reconstructed skin model of step c);
e) measuring the expression and/or activation level of at least one biological marker in the skin model of step d); and
f) determining whether said candidate cosmetic active agent, emollient or formulation is a cosmetic active agent, emollient or formulation for reducing the effects of atopic dermatitis on children's skin based on the level of step e).

The skilled person will easily understand that steps b) and c) of test A may be performed simultaneously or successively, according to need. In other words, the reconstructed skin model may be cultured in step b) in the presence of the poly(dIdC) and ILa solution and, in addition, in the presence of the cosmetic active agent, the emollient or the formulation. Alternatively, the skin model may first be cultured under conditions where it is exposed to the poly(dIdC) and ILa solution, then brought into contact with the cosmetic active agent, the emollient or the formulation.

Similarly, steps b) and c) of test B may be performed simultaneously or successively, according to the skilled person's needs. In other words, the reconstructed skin model may be cultured in step b) in the presence of at least two Th2 cytokines and, in addition, in the presence of the cosmetic active agent, the emollient or the formulation. Alternatively, the skin model may first be cultured under conditions where it is exposed to at least two Th2 cytokines, then brought into contact with the cosmetic active agent, the emollient or the formulation.

Also similarly, steps c), d) and e) of test C may be performed simultaneously or successively, according to the skilled person's needs. In other words, the reconstructed skin model may be exposed in step c) to conditions where the barrier function is impaired in the presence of at least one pathogenic bacterium and, in addition, in the presence of the cosmetic active agent, the emollient or the formulation. Alternatively, the skin model may first be exposed to conditions where it undergoes an impairment of its barrier function, before being exposed to at least one pathogenic bacterium, to finally be brought into contact with the cosmetic active agent, the emollient or the formulation.

Still similarly, steps b), c) and d) of test D may be performed simultaneously or successively, according to the skilled person's needs. In other words, the reconstructed skin model may be cultured in step b) under conditions where the barrier function is impaired and in the presence of at least one pathogenic bacterium and, in addition, in the presence of the cosmetic active agent, the emollient or the formulation. Alternatively, the skin model may first be cultured under conditions where it undergoes an impairment of its barrier function, before being exposed to at least one pathogenic bacterium, to finally be brought into contact with the cosmetic active agent, the emollient or the formulation.

The skilled person will easily understand that these different embodiments may be combined as needed. However, it is more advantageous to follow the same approach in each of the four tests. For example, if steps b) and c) of test A are performed simultaneously, it is preferable that steps b) and c) of test B are also performed simultaneously and that steps c), d) and e) of test C are also performed simultaneously and that steps b), c) and d) of test D are also performed simultaneously. On the other hand, if steps b) and c) of test A are performed successively, it is preferable that steps b) and c) of test B are also performed successively and that steps c), d) and e) of test C are also performed successively and that steps b), c) and d) of test D are also performed successively.

The candidate formulation is a formulation for preventing or reducing the effects of atopic dermatitis affecting children's skin, if said candidate formulation modulates the expression of at least one biological marker of the invention. This modulation may correspond, depending on the case, and in particular on the nature of the biological marker, to an increase or decrease in the expression of said marker. For example, it may be of interest to isolate formulations that minimize the effects of atopic dermatitis on markers preferentially expressed in stem cells, as these formulations preserve the renewal capacity of children's fragile skin. Similarly, it would be advantageous to identify formulations that minimize the effects of atopic dermatitis on barrier markers in children, in order to maintain the integrity of the skin barrier. Finally, it may be desirable to isolate formulations that do not induce markers of inflammation, in order not to accentuate the effects of the pathology.

Similarly, the candidate cosmetic active agent or emollient is a cosmetic active agent or emollient for preventing or reducing the effects of atopic dermatitis affecting children's skin, if said candidate cosmetic active agent or emollient modulates the expression of at least one biological marker of the invention. This modulation may correspond, depending on the case, and in particular on the nature of the biological marker, to an increase or decrease in the expression of said marker.

First, the cosmetic active agent, emollient or formulation of interest is brought into contact with a reconstructed skin culture obtained from a sample from a child. This bringing into contact of the cosmetic active agent or emollient of interest with the skin model may be done directly. Alternatively, it may be advantageous to formulate the cosmetic active agent or emollient of interest, for example so as to obtain a liquid composition, in order to facilitate its contact with the skin model. Therefore, according to one embodiment of the invention, the process further comprises a step of formulating the cosmetic active agent or emollient, notably in the form of a liquid, in particular aqueous, solution, prior to the step of bringing said cosmetic active agent or emollient into contact with a skin model.

The inventors have previously shown that the expression profiles of specific categories of genes (for example, barrier, inflammation, defence, stem cell genes) change with age (application WO 2014/009566). The skilled person may thus easily characterize the skin at the molecular level from birth to adulthood. More particularly, the skilled person will note that children's skin cells have a specific expression profile of genes involved in particular physiological processes, notably cell metabolism, stress response, inflammation, immunity, apoptosis, growth/proliferation and cell cycle, cell signalling, migration and differentiation, epidermal barrier, adhesion and pluripotent stem cells of the skin.

In the context of the invention, the reconstructed skin model obtained from a skin sample from a child may be any tissue model comprising skin cells, notably keratinocytes, and in which said skin cells have been obtained from a sample from a child.

For the purposes of the invention, "skin sample" means any sample containing skin cells. The skin samples according to the invention therefore include both fresh skin explants obtained directly from the patient, as well as suspended skin cell cultures, monolayer skin cell cultures, bilayer skin cell cultures and tissue models, including reconstructed skin cultures and reconstructed mucosal cultures.

As it is often difficult to work with fresh explants, it is particularly advantageous, in the context of the present invention, to use skin cell cultures. Advantageously, the skin cells according to the invention include normal, healthy or pathological cells, or cells from cell lines.

For example, the cultured skin cells may be cells obtained from a skin tissue explant. "Explant" or "skin explant" means a sample of skin cells or tissue, which may be taken for surgical purposes or for analysis.

In particular, an explant may be obtained during surgical ablation. "Ablation", as used herein, means a surgical procedure consisting in cutting out (excising) a more or less wide or deep part of the skin to treat a skin abnormality or growth. Ablation is performed either to remove a cancerous or suspicious tumour or to treat a benign skin abnormality that is a nuisance, whether for functional or aesthetic reasons. Ablation for the purposes of the invention includes, for example, skin samples obtained after plastic surgery (mammoplasty, abdominoplasty, facelift, circumcision, otoplasty, i.e. ear pinning, syndactyly or supernumerary finger, etc.).

An explant may also be obtained by biopsy. "Biopsy", as used herein, refers to a sample of skin cells or tissue taken for analysis. Several types of biopsy procedures are known and practiced in the field. The most common types include (1) incisional biopsy, in which only a sample of the tissue is taken; (2) excisional biopsy (or surgical biopsy), which consists of the total removal of a tumour mass, thus being both therapeutic and diagnostic; and (3) needle biopsy, in which a tissue sample is taken with a needle, which may be large or fine. Other types of biopsy exist, such as smears or curettage, and are also included in the present invention.

Alternatively, said skin cells may be obtained by stem cell differentiation (Guenou et al., *Lancet,* 374(9703): 1745-1753, 2009; Nissan et al., *Proc. Natl. Acad. Sci.,* 108(36): 14861-14866, 2011; Kraehenbuehl et al., *Nature Methods,* 8: 731-736, 2011).

The skin cells according to the invention, whether they come from a biopsy or are obtained by stem cell differentiation, include at least one cell type usually present in the hypodermis, dermis and/or epidermis. These cells include, among others, keratinocytes, melanocytes, fibroblasts, adipocytes, endothelial cells, mast cells, Langerhans cells and/or Merkel cells. Preferentially, the skin cells according to the invention include at least keratinocytes and/or fibroblasts. More preferentially, the skin cells according to the invention include keratinocytes and/or fibroblasts.

Many skin cell culture methods are known to the skilled person. Any of these methods may be used to culture the skin cells of the invention. Advantageously, the skin cells are cultured and/or stored under conditions that maintain, at least partially, cellular metabolism and/or cellular functions. The skin cell culture according to the invention therefore includes suspended skin cell cultures, monolayer skin cell cultures or bilayer skin cell cultures, as well as tissue models, including reconstructed skin cultures and reconstructed mucosal cultures.

For example, suspended skin cell cultures have been routinely carried out in a very large number of laboratories during the past several decades. Similarly, monolayer or bilayer skin cell cultures have been known and used for a very long time.

In addition, many tissue models, including in particular reconstructed skin models and reconstructed mucosal models (Rosdy et al., *In Vitro Toxicol.,* 10(1): 39-47, 1997; Ponec et al., *J Invest Dermatol.,* 109(3): 348-355, 1997; Ponec et al., *Int J Pharm.,* 203(1-2): 211-225, 2000; Schmalz et al., *Eur J Oral Sci.,* 108(5): 442-448, 2000; Black et al., *Tissue*

*Eng*, 11(5-6): 723-733, 2005; Dongari-Batgtzoglou and Kashleva, *Nat Protoc*, 1(4): 2012-2018, 2006; Bechtoille et al., *Tissue Eng*, 13(11): 2667-2679, 2007; Vrana et al., *Invest Ophthalmol Vis Sci*, 49(12): 5325-5331, 2008; Kinicoglu et al., *Biomaterials*, 30(32): 6418-6425, 2009; Auxenfans et al., *Eur J Dermatol*, 19(2): 107-113, 2009; Kinicoglu et al., *Biomaterials*, 32(25): 5756-5764, 2011; Costin et al., *Altern Lab Anim*, 39(4): 317-337, 2011; Auxenfans et al., *J Tissue Eng Regen Med*, 6(7): 512-518, 2012; Lequeux et al., *Skin Pharmacol Physiol*, 25(1): 47-55, 2012; EP 29 678; EP 285 471; EP 789 074; EP 1 451 302 B1; EP 1 878 790 B1; EP 1 974 718; US 2007/0148,771; US 2010/0,099,576; WO 02/070729; WO 2006/063864; WO 2006/0,63865; WO 2007/064305) are available to the skilled person.

Advantageously, the tissue model includes reconstructed skin models and reconstructed mucosal models. Preferably, the reconstructed skin model is selected from the group consisting of dermal models, containing mainly stromal cells, and more particularly fibroblasts, epidermal models consisting mainly of keratinocytes, hypodermal models, skin models comprising a dermis and an epidermis, and skin models comprising a dermis, an epidermis and a hypodermis. Models comprising at least one dermis form connective tissue, while models comprising at least one epidermis form stratified epithelia comprising the characteristic layers of the tissue in question. For example, in epidermis models, a basal layer (stratum basalis), a spinous layer (stratum spinosum), a granular layer (stratum granulosum), and a horny layer (stratum corneum) may be identified. On the other hand, the reconstructed mucosal model according to the invention is a model of mucosa of the mouth, gums, vagina or cornea.

Advantageously, said model is a connective tissue model of dermal matrix comprising a matrix support preferably selected from:

an inert support selected from the group consisting of a semipermeable synthetic membrane, in particular a semipermeable nitrocellulose membrane, a semipermeable nylon membrane, a Teflon membrane or sponge, a semi-permeable polycarbonate or polyethylene, polypropylene, polyethylene terephthalate (PET) membrane, a cellulose acetate or ester (HATF) semi-permeable Anopore inorganic membrane, a semi-permeable Biopore-CM membrane, a semi-permeable polyester membrane, a polyglycolic acid membrane or film.

This group includes for example the Skin$^2$™ ZK1100 and Dermagraft® and Transcyte® dermal models (Advanced Tissue Sciences);

a cell—culture treated plastic (forming a dermal sheet: Michel et al., In vitro Cell. Dev Biol.—Animal, 35: 318-326, 1999);

a gel or membrane based on hyaluronic acid (such as Hyalograft® 3D— Fidia Advanced Biopolymers) and/or collagen (such as an equivalent dermis or collagen lattices) and/or fibronectin and/or fibrin; this group includes for example the Vitrix® dermal model (Organogenesis);

an optionally surfaced porous matrix (for example an equivalent dermis) produced from collagen which may contain one or more glycosaminoglycans and/or possibly chitosan (EP0296078A1, WO 01/911821 and WO 01/92322).

This group also includes, for example, the Mimederm® dermal model (Coletica).

These matrix supports include stromal cells, particularly fibroblasts.

Advantageously, said skin model is an epidermis model comprising a matrix support preferably selected from:

an inert support selected from the group consisting of a semipermeable synthetic membrane, in particular a semipermeable nitrocellulose membrane, a semipermeable nylon membrane, a Teflon membrane or sponge, a semi-permeable polycarbonate or polyethylene, polypropylene, polyethylene terephthalate (PET) membrane, a cellulose acetate or ester (HATF) semi-permeable Anopore inorganic membrane, a semi-permeable Biopore—CM membrane, a semi-permeable polyester membrane;

this group includes the reconstructed epidermis models (Skinethic®) and the EpiDerm® epidermis model (Mattek Corporation);

a film or membrane based on hyaluronic acid and/or collagen and/or fibronectin and/or fibrin.

This group notably includes the skin models: Laserskin® (Fidia Advanced Biopolymers), Episkin® (L'Oreal).

These models may be seeded with fibroblasts in the dermal part.

These models, in which fibroblasts may optionally be integrated, act as a support for keratinocyte seeding and epidermal reconstitution. Advantageously, pigment cells, immunocompetent cells, nerve cells are introduced in addition to keratinocytes; preferably, the immunocompetent cells are Langerhans cells.

Advantageously, said tissue model is a reconstructed skin or mucosal tissue model comprising a dermal matrix or chorion support preferably selected from:

an inert support selected from the group consisting of a semipermeable synthetic membrane, in particular a semipermeable nitrocellulose membrane, a semipermeable nylon membrane, a Teflon membrane or sponge, a semi-permeable polycarbonate or polyethylene, polypropylene, polyethylene terephthalate (PET) membrane, a cellulose acetate or ester (HATF) semi-permeable Anopore inorganic membrane, a semi-permeable Biopore-CM membrane, a semi-permeable polyester membrane, said inert support optionally containing stromal cells, in particular fibroblasts, a gel based on collagen and/or hyaluronic acid and/or fibronectin, and/or fibrin comprising stromal cells, in particular fibroblasts, an optionally surfaced porous matrix produced from collagen which may contain one or more glycosaminoglycans and/or possibly chitosan, these porous matrices integrating stromal cells, in particular fibroblasts, a de-epidermized dermis or dead dermis, of human or animal origin.

In this group, particular mention may be made of the following skin models: Mimeskin (Coletica), EpidermFT™, EpiAirway™, EpiOccular™ EpiOral™, EpiGingival™, EpiVaginal™ (MatTek corporation), Human Corneal Epithelium (HCE), Human Oral Epithelium (HOE), Human Gingival Epithelium (HGE), Human Vaginal Epithelium (HVE))(Skinethic®, Phenion® Full Thickness Skin Model (Phenion) Apligraf® (Organogenesis), ATS-2000 (CellSystems® Biotechnologie Vertrieb) as well as Skin 2TM (ZK1200-1300-2000 Advanced Tissue Science).

Furthermore, skin models specifically intended for tissue therapy are available which may also be used within the scope of the present invention. Mention may be made of the Epidex® (Modex Therapeutiques), Epibase® (Laboratoire Genevrier), Epicell™ (Genzyme), Autoderm™ and Transderm™ (Innogenetics) models.

The matrix support is then seeded with keratinocytes to reconstruct the epidermis and finally obtain a reconstructed skin.

Advantageously, the skin model used includes a model in which at least one complementary cell type has been incorporated, such as endothelial cells (EC) and/or immune cells such as lymphocytes, macrophages, mast cells, dendritic cells and/or fat cells and/or skin appendages, such as head and body hair, sebaceous glands.

After exposing the reconstructed skin model of the invention to at least one cytokine, the skilled person can measure the expression level of the biological markers of the invention.

"Biological marker", for the purposes of the present application, refers to a characteristic that is objectively measured and evaluated as an indicator of normal biological processes, pathogenic processes, or pharmacological responses to a therapeutic intervention. A biological marker therefore refers to a whole range of different substances, activities and parameters. For example, a biological marker may be a substance whose detection indicates a particular disease state (for example the presence of reactive C protein as a marker of infection), or conversely a substance whose detection indicates a specific physiological state. Alternatively, the biological marker according to the invention may be a parameter, which is for example characteristic of a particular disease state. Such a parameter is for example the activity of the skin to inhibit the proliferation of pathogenic bacteria or the formation of a biofilm by these bacteria. The biological marker according to the invention is preferentially a gene, gene products such as transcripts, peptides from these transcripts, a lipid, a sugar or a metabolite, or a physiological activity of the skin model.

According to one embodiment of the present invention, the biological marker is a gene, gene products such as transcripts or peptides, a lipid, a sugar or a metabolite or an activity whose changes in expression and/or activation, in particular in expression and/or activation level, correlate with a physiological state of children's skin.

The skilled person seeking to determine to which class a gene or protein marker belongs will be able to easily consult the relevant scientific literature or refer to public databases such as, for example, those contained in the National Center for Biotechnology Information website (www.ncbi.nlm.nih.gov/guide).

The inventors have particularly selected markers whose variation in expression and/or activation level varies in a surprising and unexpected way in children's atopic skin. The selected markers are therefore of particular interest in the context of the method of the invention, insofar as their expression and/or activation level is measured on a skin model reproducing the characteristics of children's skin in at least one of the phases of atopic dermatitis.

In particular, the inventors have shown that the markers of inflammation are particularly expressed after children's atopic skin has been infected with pathogenic bacteria. Inflammation is a normal defence reaction of the body, but it may contribute to the reduction of skin integrity. In addition, the inventors have shown that, at the same time, there is a decrease in the expression and/or activation of markers leading to a strengthening of the barrier. Furthermore, stem cell markers are also affected and consequently so is the skin's renewal capacity. On the other hand, bringing the skin into contact with a formulation active against the effects of atopic dermatitis on children's skin makes it possible to prevent and correct the variations in expression and/or activation of said markers, which underlines their relevance. Finally, atopic infant skin had reduced activity in inhibiting the proliferation of pathogenic bacteria. Similarly, the activity that inhibits biofilm formation by these same bacteria is reduced in the skin of children with atopic dermatitis.

The biological marker of the invention is therefore advantageously a marker selected from the group of activities that inhibit bacterial physiology, markers of immunity, of skin inflammation, of the barrier function and markers preferentially expressed in stem cells.

According to a first preferred embodiment, the biological marker of the invention is a bacterial physiology-inhibiting activity. More particularly, said biological marker is an activity that inhibits the proliferation of pathogenic bacteria. Indeed, it is known that said pathogenic bacteria, notably staphylococci and streptococci, are only slightly able, if at all, to proliferate on healthy skin, while they are able to become established and multiply on atopic skin. This activity may be measured simply by a bacterial count. For example, a defined number of bacteria may be inoculated on the reconstituted skin model of the invention and the remaining number of bacterial cells is determined after a specified time or at regular intervals.

Alternatively, the biological marker is an activity that inhibits the formation of a biofilm by pathogenic bacteria. "Biofilm", as used herein, refers to a type of microorganism organization in which cells adhere to a surface. Most often, biofilms are characterized by the secretion of an adhesive and protective exopolymeric matrix. In a biofilm, the microorganisms and, in particular, the bacteria, notably including staphylococci and streptococci, are in "sessile" form, i.e. attached to the surface and living in a community. Many microorganisms, including pathogenic bacteria such as those described above, form biofilms. Furthermore, it is considered that this is the microorganisms' natural way of life. The biofilm's structure and physiology would give the constitutive microorganisms social organization conditions similar to those established between eukaryotic cells within tissues. Thus, biofilms act as reservoirs of several species of microorganisms and provide them with protection against external attacks, such as disinfectants, antibiotics, antiseptics, via the extracellular matrix (Tremblay et al., *Can J Vet Res.* 2014; 78(2): 110-116).

A biofilm according to the invention may include one or more microorganism species. Preferentially, the biofilm according to the invention includes cells of at least one pathogenic bacterial species as described above. More preferentially, the biofilm according to the invention comprises only cells of pathogenic bacteria. Even more preferentially, the biofilm according to the invention consists of cells of a single species of pathogenic bacterium.

The biofilm-inhibiting activity can for example be measured by monitoring under a microscope, notably a scanning electron microscope, formation of the biofilm on the surface of the atopic skin model of the invention.

This approach has made it possible to differentiate formulations according to their ability to restore one and/or the other of these inhibitory activities, as shown in the experimental examples.

According to a particularly preferred embodiment, the method of the invention is characterized in that the bacterial physiology-inhibiting activity is selected from inhibition of bacterial proliferation and inhibition of biofilm formation.

The biological marker according to the invention may also be a marker of immunity, of the barrier function, of inflammation or of stem cells.

"Marker of immunity", as used herein, refers to all markers used to determine the identity of the organism and to defend it from without. These markers serve as the first line of defence against bacterial infections. A marker of immunity according to the invention is preferably beta-defensin 2 or Toll-like receptor 2.

Beta-defensin 2 (BD-2), which is also called skin-antimicrobial peptide 1 (SAP1), is a peptide encoded by the DEFB4 gene (NCBI reference: Gene ID: 1673). The sequence of human beta-defensin 2 is available under accession number NP_004933, while the DEFB4 gene sequence is available under accession number NM_004942.

The Toll-like receptor 2 (TLR2) protein (sequence NP_003255.2) is a membrane receptor expressed on the surface of certain cells. It recognizes foreign substances, notably bacterial lipoproteins. TLR2 activation leads to the synthesis of cytokines, notably interleukin 6. TLR2 is encoded by the TLR2 gene (NCBI reference: Gene ID: 7097; sequence: NM_003264).

The present inventors have shown, in the atopic dermatitis models developed, a decrease in the expression of markers of innate immunity. It is known in the literature that the skin in atopic dermatitis has a deficit of innate immunity: antimicrobial peptides such as beta-defensin 2 are deficient, as is the TLR2 receptor whose expression within the epidermis is decreased in atopic dermatitis (The Etiology of Atopic Dermatitis, Edition: 1st, Chapter: Chapter Two: Microbiology of Atopic Dermatitis, Publisher: Springer, Editors: Herbert B. Allen). The reduction of these markers in the models developed therefore makes it possible to validate the models with regard to atopic dermatitis pathophysiology.

The present inventors have also shown, in the atopic dermatitis models developed, an increase in the expression of markers of inflammation. This increase therefore makes it possible to validate the models with regard to atopic dermatitis pathophysiology.

"Markers of inflammation", for the purposes of the invention, means markers whose variation in expression correlates with skin inflammation.

"Inflammation", according to the invention, refers to all reactive defence mechanisms by which the body recognizes, destroys and eliminates all foreign substances. "Skin inflammation" refers more specifically to a reaction of the immune system in response to an insult to the skin, such as an environmental insult, which may or may not cause a wound, or vascular damage if applicable. Skin inflammation is accompanied by a variation in the expression or concentration level of gene or protein markers well known to the skilled person, who may refer, for example, to Vahlquist (*Acta Derm Venereol;* 80: 161; 2000).

The triggering and continuation of inflammation, its spread from the initial site, requires factors that are synthesized locally or that exist as inactive precursors in the circulation. Depending on the type of mediators synthesized, it is possible to differentiate particular processes in the inflammation reaction. For example, skin inflammation includes in particular the production, in response to external insult, of protein inflammatory mediators, such as cytokines IL-1, IL-2, IL-6, IL8, TNFα and TSLP, the complement system, or proteins involved in coagulation, if applicable. Protein mediators will induce a cascade of reactions within the skin involving other inflammation cells, in particular immune and vascular cells. The clinical result is expressed as redness or oedema.

Preferably, the mediator of inflammation is selected from the group consisting of CCL2, CXCL1, CCL7, IL6, IL18, CCL3, CCL5, CCL7, KLK5 and TSLP. CCL2 (sequence: NP_002973.1), CCL3 (sequence: NP_002974.1), CCL5 (sequence: NP_002976.2) and CCL7 (sequence: NP_006264.2) are chemokine cytokines and more particularly C—C motif chemokines. They are encoded by the CCL2 (NCBI reference: Gene ID: 6347; sequence: NM_002982.3), CCL3 (NCBI reference: Gene ID: 6348; sequence: NM_002983), CCL5 (NCBI reference: Gene ID: 6352; sequence: NM_002985) and CCL7 (NCBI reference: Gene ID: 6354; sequence: NM_006273) genes, respectively. In addition, CXCL1 (sequence: NP_001502.1) is also a chemokine, but with a C—X—C motif. It is encoded by the CXCL1 gene (NCBI reference: Gene ID: 2919; sequence: NM_001511).

Human IL-6 and IL-8 interleukins are pro-inflammatory cytokines. The protein sequence of the first corresponds to the reference sequence NCBI: NP_000591.1. This protein is encoded by the human IL6 gene (NCBI reference: Gene ID: 3569). Its sequence is accessible under the reference NCBI: NM_000600. The IL-8 protein, in turn, has a sequence corresponding to an NCBI reference selected from: NP_001230140.1, NP_001553.1 and NP_001230140.1. This protein is encoded by the human IL8 gene (NCBI reference: Gene ID: 3606). Its sequence is accessible under one of the NCBI references: NM_001562.3 and NM_001243211.1.

The cytokine thymic stromal lymphopoietin or TSLP (sequence: NP_149024.1 or NP_612561.2). This protein, encoded by the TSLP gene (NCBI reference: Gene ID: 85480) with the sequence NM_033035 or NM_138551, has an important role in the maturation of T cell populations through the activation of antigen-presenting cells and, by being involved in the Th2 orientation of T cells, constitutes a key factor in atopic dermatitis pathophysiology.

Kallikrein-related peptidase 5, also called stratum corneum tryptic enzyme, with sequence NP_036559.1, is encoded by the KLK5 gene (NCBI reference: Gene ID: 25818) which itself has the sequence NM_012427. This serine protease regulates desquamation by degrading the proteins forming the extracellular component of stratum corneum cell junctions. The increase in desquamation corresponds to a reduction in barrier efficacy, as the junctions are less watertight. KLK5 expression level and activity are overexpressed in atopic dermatitis skin, which exacerbates barrier function impairment (desquamation) and also promotes inflammatory processes and induction of pruritus via PAR2 activation.

The present inventors have also shown, in the atopic dermatitis models developed, a reduction in the expression or quantity of barrier function markers and markers preferentially expressed in stem cells. Impaired barrier function is a well-known feature of atopic dermatitis pathophysiology. Thus, the induction of a reduction in barrier function markers validates the models as representative of atopic dermatitis. However, it had never before been shown that the expression of markers preferentially expressed in stem cells is inhibited, either in a model of atopic dermatitis or in atopic dermatitis pathophysiology. This is therefore a discovery and a specific feature of atopic dermatitis skin in babies.

The "barrier markers" according to the invention include markers that are specifically expressed in the outermost layers of the epidermis and that participate in barrier function.

As the skilled person well knows, the main function of the skin is to establish a protective barrier against environmental insults while allowing certain exchanges between the internal and external environment. This barrier function is mainly provided by the stratum corneum of the epidermis. Intercellular lipids and corneodesmosomes as well as the corneal envelope of corneocytes are the key components.

However, under the stratum corneum, the tight junctions constitute a second line of barrier function. At the stratum granulosum, these junctions constitute a selective paracellular diffusion barrier which prevents the penetration of harmful molecules.

Tight junctions are composed of different transmembrane proteins such as claudins, occludin and ZO1 in particular.

The barrier functions provided by the stratum corneum and the tight junctions are closely related. Indeed, the impairment of one can influence the formation of the other.

Preferentially, the markers of barrier function according to the invention are markers expressed or present in the stratum corneum or markers expressed or present in the tight junctions of the stratum granulosum. In a more preferential embodiment, said epidermal barrier marker is selected from the group consisting of keratin 1 (KRT1), desmoglein 1 (DSG), involucrin (IVL), sciellin (SCEL), sphingomyelinase (SMPD1), caspase 14 (CASP14), loricrin (LOR), filaggrin (FLG), transglutaminase 1 (TGM1), claudin 1 (CLDN1), natural moisturizing factors (NMF) and ceramides.

The KRT1 gene (Gene ID: 3848; NM_006121) encodes keratin 1 (NP_006112.3). Like keratin 10 (NP_000412.3), which is encoded by the KRT10 gene (Gene ID: 3858; NM_000421), keratin 1 is a constituent of the intracellular network of keratinocytes and, as such, participates in the general structure of the stratum corneum. The BARX2 gene (Gene ID: 8538; NM_003658.4) encodes the transcription factor Barx2 (NP_003649.2) which regulates adhesion during epidermal formation and differentiation.

The corneodesmosome is the only junction structure of the corneal layer, which underlines the importance of this structure for maintaining the integrity of the corneal layer.

Corneodesmosin (CDSN) (Simon et al., *J Biol Chem*, 272: 31770-31776, 1997; Simon et al., J Biol Chem, 276: 20292-20299, 2001) is a specific marker of corneodesmosomes, as it is the only protein specifically located in the extracellular part of corneodesmosomes (Jonca et al., *The Open Dermatology Journal*, 4: 36-45, 2010; Jonca et al., *Eur J Dermatol*, 21 (Suppl 2): 35-42, 2011). The term corneodesmosin, as used herein, refers to the human protein having a sequence represented by NP_001255, and encoded by the CDSN gene (Gene ID: 1041; NM_001264).

Desmoglein 1 is a constitutive protein of corneodesmosomes whose sequence is available under reference NP_001933. The DSG1 gene (Gene ID: 1828) encodes desmoglein-1 and has the reference sequence NM_001942. Involucrin, whose peptide sequence is the reference sequence NCBI: NP_005538.2, is expressed in the spinous-granular layers. It is the first precursor of the corneal envelope which represents 5 to 15% of the corneal envelope, and also serves as a link with the corneal lipid envelope. It is encoded by the IVL gene (Gene ID: 3713), whose sequence has reference NCBI: NM_005547.2. Sciellin, with sequence NP_001154178, and encoded by the SC gene (Gene ID: 8796), which itself has the sequence corresponding to the reference NCBI: NM_001160706, is a precursor of the corneal envelope. Loricrin is a major protein component of the corneal envelope, of which it represents about 70% by mass. This protein has the sequence NP_000418 and is encoded by the LOR gene (Gene ID: 4014) with a sequence corresponding to the reference NCBI: NM_000427. Bonds between the protein components of the corneal envelope are formed by the enzyme transglutaminase 1. The sequence of this enzyme corresponds to the one found under the reference NP_000350. The TGM1 gene (NCBI reference: Gene ID: 7051) encodes desmoglein-1 and has the reference sequence NM_000359.

Sphingomyelinase (SMase), or sphingomyelin diesterase, is a hydrolase involved in sphingolipid metabolism. It cleaves sphingomyelin into phosphocholine and ceramides 2 and 5, which are part of the intercellular lipid matrix that ensures the watertightness of the stratum corneum. Sphingomyelinase is a protein whose sequence is represented by the reference NCBI: NP_000534. The gene encoding this enzyme is the SMPD gene (NCBI reference: Gene ID: 6609) with a sequence corresponding to NM_000543. Glucosylceramidase (NP_000148.2), also known as acid β-glucosidase, β-glucocerebrosidase and D-glucosyl-N-acylsphingosine glucohydrolase, is another hydrolase involved in sphingolipid metabolism. It catalyses cleavage of the bond between the ceramide unit and the glucose residue of glucocerebrosides, thus contributing to the synthesis of ceramides. This enzyme is encoded by the GBA gene (Gene ID: 2629), whose sequence corresponds to the reference NM_000157. The LASS6 gene (Gene ID: 253782), also known as CERS6, encodes ceramide synthetase 6 (NP_001243055.1) which also is involved in ceramide synthesis. The sequence of the LASS6 gene is the sequence represented by NM_001256126.

Tight junctions represent one mode of cellular adhesion in epithelial tissues, They block the circulation of fluids between cells and thus ensure watertightness between two tissue compartments. They are located at the apex of epithelial cells where they form a continuous surrounding band to provide watertightness. The CLDN 1 gene (NCBI reference: Gene ID: 9076) encodes the claudin 1 protein which is one of the most important components of tight junctions. This protein has a sequence corresponding to the one whose NCBI reference is NP_066924. The sequence of the CLDN1 gene is accessible under the reference NM_021101.

Barrier markers also include markers of metabolism of NMF and of intercorneocyte lipids, such as ceramides. These compounds retain water in the epidermis as it ascends to the corneal layer. In the corneal layer, lipids are arranged in a lamellar plane in the space between corneocytes, thus forming a cement that helps protect the skin against external insults and maintain a proper level of intraepidermal water. These lipids are phospholipids, cholesterol and glucosylceramides, which are modified in the intercorneocyte space, by specialized enzymes, into ceramides, cholesterol, cholesterol sulphate and free fatty acids. (Jungerstend et al., *Contact Dermitis*, 58(5): 255-262, 2008). Thus, the acid sphingomyelinase and beta glucocerebrosidase enzymes transform intercorneocyte lipids into ceramides 2 and 5 (for sphingomyelinase) and into ceramides 1, 3, 4, 6, 7, 8 and 9 (for glucocerebrosidase).

Natural moisturizing factor (NMF) is derived from the proteolysis of filaggrin according to a cascade of reactions involving enzymes notably including caspase 14 and peptidylarginine deiminase (PAD1). NMF is a mixture of hygroscopic substances with water-retaining properties (Fluhr et al., *Exp Dermatol.*, 19(6): 483-492, 2010). Among these, the most hygroscopic substances are the sodium salt of pyrrolidone carboxylic acid or PCA Na (from the cyclization of glutamic acid released by the decomposition of profilaggrin) and lactates. NMF also contains free amino acids (serine, citrulline, etc.), citrates and formates, urea, ions, nitrogen, uric acid, glycosamine, creatinine, phosphates, as well as yet unidentified compounds. The amount of NMF can be measured by all methods known to the skilled person, notably by Raman microspectroscopy.

Filaggrin (NCBI: NP_002007.1) is encoded by the human FLG gene (NCBI reference: Gene ID: 2312). Filaggrin aggregates with the keratin fibres of the cytoskeleton, thus reducing corneocytes to flattened discs; this intracellular network confers resistance and protection to the stratum corneum. On the other hand, its degradation leads to the formation of the constituents of the NMF. Caspase-14 is a member of the caspase family that is necessary for the degradation of filaggrin to NMF (Hoste et al., *J Invest Dermatol.* 131(11): 2233-2241, 2011). This protein, with sequence NP_036246, is encoded by the CASP14 gene (NCBI reference: Gene ID: 23581) whose sequence is found under reference NM_012114.

Filaggrin and its NMF derivatives are particularly well known to be deficient in atopic dermatitis skin and constitute a major factor in atopic dermatitis pathophysiology, which confirms that the models developed by the inventors accurately reproduce atopic dermatitis pathophysiology.

The "markers preferentially expressed in stem cells" according to the invention include the markers, and more specifically the genes and the proteins, which are specifically present in epidermal stem cells.

For the purposes of the invention, "stem cell of the epidermis" or "epidermal stem cell" means an epidermal cell capable of long-term renewal. The epidermal stem cells of the invention include, among others, follicular stem cells, sebaceous stem cells and basal stem cells, the latter also being called interfollicular epidermal stem cells. "Follicular stem cells", "sebaceous stem cells" and "basal stem cells", for the purposes of the invention, are the stem cells located in the region of the hair follicle bulge, in the sebaceous glands and in the basal layer of the epidermis, respectively. In a preferential embodiment of the invention, the epidermal stem cells of the invention are basal stem cells.

More precisely, an epidermal stem cell, for the purposes of the present invention, is a cell endowed with a high potential for long-term renewal. "Potential for renewal", as used herein, refers to the ability to undergo at least one cycle of cell division. A "high potential for long-term renewal" is therefore the ability of a cell to enter several successive cycles of cell division. It is well known that the differentiated cells of the skin are not capable of undergoing several successive divisions (Fortunel and Martin, *J Soc Biol,* 202 (1): 55-65, 2008). It is understood herein that "successive" does not mean "consecutive" and that there may be periods during which a stem cell according to the invention remains quiescent without however losing its high potential for long-term renewal.

Conservation of a high potential for long-term renewal is expressed by asymmetric division producing two different cells. The first daughter cell is a stem cell identical to the parent stem cell, while the second is a transit amplifying cell that divides in a limited manner over a short period of time and then enters the differentiation process. Advantageously, the epidermal stem cells of the invention are therefore also capable of generating at least one type of epidermal cell by differentiation. In other words, the transit amplifying cell is capable of giving rise to at least one type of epidermal cell by differentiation. Preferentially, said epidermal cell is a keratinocyte. More preferentially, the transit amplifying cell is able to give rise all types of epidermal cells by differentiation.

Preferentially, the markers expressed in stem cells are markers that participate in the functions and protection of stem cells. Examples include the markers ΔNp63, BIRC5 (survivin), FN1 (fibronectin 1), MCSP (melanoma-associated chondroitin sulphate proteoglycan), LRIG1 (leucine-rich repeats and immunoglobulin-like domains protein 1), GJA1 (connexin 43), NID1 (nidogen 1), KRT15 (keratin 15), KRT19 (keratin 19), EGFR (epidermal growth factor receptor), CD71 (transferrin receptor), DSG3 (desmoglein 3), ITGB1BP1 (integrin beta1 binding protein), ITGA6 (integrin alpha 6), ITGB1 (integrin beta1) and ITGB4 (integrin beta 4) or markers involved in the signalling and regulation of stem cell activity such as Wnt/beta catenin, sonic hedgehog (SHH), NOTCH1 (Notch homolog 1, translocation-associated). ΔNp63 and survivin are markers of resistance to apoptosis, thus having a role in stem cell survival. Cytokeratins 15 and 19 are positive stem cell markers, cytokeratin 15 being a marker of stem cell survival. MCSP colocalizes with integrins in non-dividing cells, while integrin beta1 (marker of basal membrane adhesion to the extracellular matrix) and integrin alpha 6 (constituting hemi-desmosomes, marker of inter-keratinocyte binding) are surface proteins that participate in intercellular communication, regulate differentiation/proliferation processes and interaction with the niche. The transferrin receptor CD71 is a known surface marker of stem cells, which is used to isolate, in a population of integrin-alpha6 positive cells, cells with high clonogenicity. Finally, Lrig1 is an epidermal growth factor receptor (EGFR) antagonist, thus maintaining stem cells quiescent, while, in contrast, EGFR, which is a marker whose absence characterizes stem cells, leads cells down the proliferation pathway.

Preferentially, the marker preferentially expressed in the stem cells of the invention is selected from the group consisting of markers KRT15 (keratin 15), KRT19 (keratin 19), NOTCH1 (Notch homolog 1), BIRC5 (survivin), ITGA6 (integrin alpha 6), ITGB1 (integrin beta1) and ITGB4 (integrin beta 4). These markers are well known to the skilled person. The KRT15 (NCBI reference: Gene ID: 3866), KRT19 (NCBI reference: Gene ID: 3880), NOTCH1 (NCBI reference: Gene ID: 4851), BIRC5 (NCBI reference: Gene ID: 332), ITGA6 (NCBI reference: Gene ID: 3655) and ITGB1 (NCBI reference: Gene ID: 3688) genes thus correspond to the sequences represented by following GenBank accession numbers: NM_002276, NM_001012270, NM_017617, NM_015541, NM_000210, NM_002211 and NM_000213, respectively. The keratin 15, keratin 19, Notch homolog 1, survivin, integrin alpha 6 and integrin beta1 proteins correspond to the sequences represented by the following GenBank accession numbers: NP_002266, NP_002267, NP_060087, NP_001012270, NP_000201 and NP_002202, respectively.

According to a particularly preferred embodiment, the method of the invention is characterized in that:
 the marker of immunity is HBD2 or TLR2,
 the marker of inflammation is CCL2, CXCL1, CCL7, IL6, IL18, CCL3, CCL5, CCL7, KLK5 or TSLP,
 the marker of barrier function is FLG, KRT1, KRT10, SCEL, BARX2, LOR, IVL, TGM1, DSG1, CDSN, CLDN1, CASP14, SMPD1, GBA, LASS6, NMF or the ceramides, or
 the marker preferentially expressed in stem cells is KRT15, KRT19, NOTCH1, BIRC5, ITGA6, ITGB1 or ITGB4.

Furthermore, it will be evident to the skilled person that the method of the invention will allow an evaluation of the efficacy of the formulation or the active agent which will be all the more complete when a large number of markers of different types are used.

According to a preferred embodiment, the method of the invention comprises a step of measuring the expression level of a combination of biological markers, in step d) of tests A and B, step f) of test C, and step e) of test D include. Said combination according to the invention comprises at least two markers, said markers being selected from at least two different categories of markers described above: markers of activities that inhibit bacterial physiology, of immunity, of skin inflammation, of the barrier function and markers preferentially expressed in stem cells. According to a preferred embodiment, said combination comprises more than two markers. According to a more preferred embodiment, each of the markers belongs to a different category of markers described above. It is also possible to use combinations of markers as defined above, in which certain marker classes are represented by more than one marker.

The use of combinations of markers comprising at least one marker of each of the different types indicated above is particularly advantageous.

For each of the biological markers described above, the term "expression level" refers to the cellular concentration of said marker. Thus, the expression level of lipids, such as ceramides, corresponds to the concentration of said lipids in the cell. Similarly, the expression level of a protein corresponds to the concentration of said protein in the cell. If the marker is a gene, the "expression level" for the purposes of the invention corresponds to the cellular concentration of at least one of the products of the gene of said marker. More precisely, the expression level of said biological marker corresponds to the quantity or the cellular concentration of the transcript of said gene or of the protein derived from said transcript. According to a preferred embodiment, the expression level of said biological marker corresponds to the quantity or the cellular concentration of the transcript of said gene. According to another embodiment, the expression level of said biological marker corresponds to the quantity or the cellular concentration of the protein derived from said transcript. According to another embodiment, the expression level of said biological marker corresponds to the quantity or the cellular concentration of the lipid.

For the purposes of the present application, "measuring of the expression level of a combination of biological markers" means measuring the expression level of each of the markers of the combination. The expression of a gene can be measured for example at the nucleotide level, by measuring the quantity of transcripts of said gene, and can also be measured for example at the peptide level, by measuring the quantity of proteins derived from said transcripts. Thus, "measuring the expression level of said gene", for the purposes of the invention, means measuring the quantity of product of the gene in its peptide or nucleotide form.

In general, expression of the biological marker according to the invention will be detected in vitro from the reconstructed skin model.

In a particular embodiment, the method of the invention may comprise one or more intermediate steps between obtaining the reconstructed skin model and measuring the expression of the biological marker, said steps corresponding to extracting from said reconstructed skin model a lipid sample, an NMF sample, an mRNA sample (or the corresponding cDNA) or a protein sample. This may then be used directly to measure expression of the marker. The preparation and extraction of mRNA (as well as the reverse transcription thereof to cDNA), of proteins, of lipids or of NMF from a sample of skin cells are routine procedures well known to the skilled person.

Once a sample of mRNA (or corresponding cDNA) or protein is obtained, expression of the marker in terms either of mRNA (i.e. all mRNAs or cDNAs present in the sample) or of proteins (i.e. all proteins present in the sample) can be measured. The method used to that end then depends on the type of transformation (mRNA, cDNA or protein) and the type of sample available.

When expression of the marker is measured at the mRNA (or corresponding cDNA) level, any technology usually used by the skilled person can be employed. These technologies for analysing the level of gene expression, such as transcriptome analysis, include well-known methods such as PCR (polymerase chain reaction, if starting from DNA), RT-PCR (reverse transcription-PCR, if starting from RNA) or quantitative RT-PCR or nucleic acid microarrays (including DNA microarrays and oligonucleotide microarrays) for a higher throughput.

The term "nucleic acid microarrays", as used herein, refers to several different nucleic acid probes attached to a substrate, which may be a microchip, a glass slide, or a bead the size of a microsphere. The microchip may be made of polymers, plastics, resins, polysaccharides, silica or a silica-based material, carbon, metals, inorganic glass, or nitrocellulose.

The probes may be nucleic acids such as cDNA ("cDNA microarray"), mRNA ("mRNA microarray") or oligonucleotides ("oligonucleotide microarray"), said oligonucleotides which may typically have a length comprised between about 25 and 60 nucleotides.

To determine the expression profile of a particular gene, a nucleic acid corresponding to all or part of said gene is labelled and then brought into contact with the microarray under hybridization conditions, leading to the formation of complexes between said labelled target nucleic acid and the probes attached to the surface of the microarray complementary to that nucleic acid. The presence of labelled hybrid complexes is then detected.

These technologies make it possible to monitor the expression level of a particular gene or of several genes or even of all genes in the genome (full genome or full transcriptome) in a biological sample (cells, tissues, etc.). These technologies are routinely used by the skilled person and therefore there is no need to detail them here. Exemplary embodiments of the invention based on gene expression analysis (cDNA microarrays) and on quantitative PCR are described in the experimental section.

Alternatively, it is possible to use any current or future technology for determining gene expression based on the amount of mRNA in the sample. For example, the skilled person can measure gene expression by hybridization with a labelled nucleic acid probe, such as Northern blot (for mRNA) or Southern blot (for cDNA), but also by techniques such as the serial analysis of gene expression (SAGE) method and derivatives thereof, such as LongSAGE, SuperSAGE, DeepSAGE, etc. It is also possible to use tissue microarrays (TMAs). The tests usually used with tissue microarrays include immunohistochemistry and fluorescence in situ hybridization. For analysis of mRNA level, tissue microarrays may be coupled to fluorescence in situ hybridization. Finally, it is possible to use massive parallel sequencing to determine the amount of mRNA in the sample (RNA-Seq or "whole-transcriptome shotgun sequencing"). To that end, several massive parallel sequencing methods are available. For example, such methods are described in U.S. Pat. Nos. 4,882,127; 4,849,077; 7,556,922; 6,723,513; WO 03/066896; WO 2007/111924; US 2008/0020392; WO 2006/084132; US 2009/0186349; US 2009/0181860; US 2009/0181385; US 2006/0275782; EP-B1-1141399; Shendure Et Ji, *Nat Biotechnol*, 26(10): 1135-45. 2008; Pihlak et al., *Nat Biotechnol*, 26(6): 676-684, 2008; Fuller et al., *Nature Biotechnol*, 27(11): 1013-1023, 2009; Mardis, *Genome Med*, 1(4): 40, 2009; Metzker, *Nature Rev. Genet.*, 11(1): 31-46, 2010.

When expression of the marker is measured at the protein level, specific antibodies may be used, particularly in well-known technologies such as immunoprecipitation, immunohistology, western blot, dot blot, ELISA or ELISPOT, protein microarrays, antibody microarrays, or tissue microarrays coupled to immunohistochemistry. Other techniques that may be used include FRET or BRET techniques, microscopy or histochemistry methods, including confocal and electron microscopy methods, methods based on the use of one or more excitation wavelengths and a suitable optical method, such as an electrochemical method (voltammetry and amperometry techniques), atomic force microscopy, and radiofrequency methods, such as multipolar, confocal and non-confocal resonance spectroscopy, detection of fluorescence, luminescence, chemiluminescence, absorbance, reflectance, transmittance, and birefringence or refractive index (for example, by surface plasmon resonance, by ellipsometry, by resonant mirror method, tec.), flow cytometry, radioisotopic or magnetic resonance imaging, polyacrylamide gel electrophoresis analysis (SDS-PAGE); by HPLC-mass spectrophotometry, by liquid chromatography/mass spectrophotometry/mass spectrometry (LC-MS/MS). All these techniques are well known to the skilled person and it is not necessary to detail them here.

If the biological marker is a lipid, notably a ceramide, the skilled person may use all available methods to measure the lipid content in a skin cell sample. These methods include, among others, liquid chromatography (HPLC, see for example Sullivan et al., *Arch Ophthalmol.*, 120(12): 1689-99, 2002), for example coupled to an evaporative light diffraction detector (HPLC-ESD, see Nordbäck et al., *J. High Resolut. Chromatogr.*, 22: 483-486, 1999; Torres et al., *J. Chromatogr. A.*, 1078: 28-34, 2005); thin layer chromatography (TLC, for example Downing et al., *J Invest Dermatol.*, 77(4): 358-360, 1981; Nordstrom et al., *J Invest Dermatol.*, 87(2): 260-263, 1986); nuclear magnetic resonance (NMR, see for example Robosky et al., *J Lipid Res.*, 49(3): 686-692, 2008); in vivo confocal Raman microspectroscopy; mass spectrometry, gas chromatography coupled to mass spectrometry (GC-MS, see O'Neill et al., *J Chromatogr Sci.*, 14(1): 28-36, 1976); gas chromatography coupled to a flame ionization detector; liquid chromatography coupled to mass spectrometry (see for example van Smeden et al., *J Lipid Res*, 52(6):1211-1221, 2011); ultra-performance liquid chromatography (UPLC, see Rainville et al., *J Proteome Res.*, 6(2):552-558, 2007; Castro-Perez et al., *J Proteome Res.*, 10(9): 4281-4290, 2011). The organization of these lipids in the skin and more particularly in the stratum corneum (or corneal layer), lamellar or lateral organization, can also be analysed by techniques such as X-ray diffraction (Bouwstra et al., *J Invest Dermatol.*, 97(6): 1005-1012, 1991; van Smeden et al., *J Lipid Res.*, 52(6): 1211-1221, 1991) or by Fourier transform infrared spectroscopy (Gorcea et al., *Int J Pharm.* Nov. 10, 2011.) or by morphometric analysis using electron microscopy (Daehnhardt-Pfeiffer et al., *Skin Pharmacol Physiol.*, 25(3): 155-161, 2012) or by electron microscopy analysis of the vitreous skin section combined with molecular analysis (Iwai et al., *J Invest Dermatol.*, Apr. 26, 2012).

Measuring NMF concentration is a procedure well known to the skilled person. In particular, it is possible to measure NMF using in vivo confocal Raman microspectroscopy. It is a procedure commonly used in the field for at least 15 years. Examples include publications by Caspers et al. (*J Invest Dermatol.*, 116(3): 434-442, 2001), Vyumvuhore et al. (*J Biomed Opt.*, 19(11): 111603, 2014) and Falcone et al. (*Skin Pharmacol Physiol*, 28: 307-317, 2015). It is also possible to measure NMFs by liquid chromatography coupled to mass spectrometry. Examples include Piraud et al. (*Rapid Commun Mass Spectrom,* 19(12):1587-602, 2005), Petritis et al. (*Journal of Chromatography A,* 833(2): 147-155, 1999), Henriksen et al. (*J Am Soc Mass Spectrom,* 16(4): 446-455, 2005) and Yang (Application of biophysics and bioengineering to the assessment of skin barrier function. Thesis (Doctor of Philosophy (PhD)). University of Bath, U K, 2011).

In a particular embodiment, the expression level of said biological marker of step d) of test A is compared with a reference expression level. According to another particular embodiment, the expression level of said biological marker of step d) of test B is compared with a reference expression level. According to yet another particular embodiment, the expression level of said biological marker of step f) of test C is compared with a reference expression level. Still according to a particular embodiment, the expression level of said biological marker of step e) of test D is compared with a reference expression level.

"A reference expression level of a biological marker" means, for the purposes of the present application, any expression level of said marker used as a reference. For example, a reference expression level may be obtained by measuring the expression level of the marker of interest in a children's skin model under specific conditions. The skilled person will be able to choose these particular conditions based on his or her objective when implementing the invention.

According to another embodiment, the reference expression level of a biological marker is the expression level of said marker obtained in a children's skin model, brought into contact with a reference formulation or active agent, and exposed to atopic dermatitis conditions according to at least one of the tests A, B, C or D described above.

When the reference expression level is an expression level obtained in a skin model exposed to atopic dermatitis conditions according to at least one of the tests A, B, C or D, the skilled person will easily understand that the atopic dermatitis conditions of the skin model used in the method of the invention and of the model used to obtain a reference expression level are preferentially identical. Thus, preferentially, the conditions used to generate atopic dermatitis, for example the pathogenic bacterium responsible for infection in tests C and D, as well as the duration of exposure used in the method of the invention and the model used to obtain a reference expression level are preferentially identical.

For example, the skilled person may use as reference formulation any formulation of the prior art known for its effect in preventing or treating atopic dermatitis in children's skin.

| PRODUCT 1: Balm-type oil/water (o/w) emulsion | |
|---|---|
| EU INCI | % INCI |
| AQUA | QS |
| GLYCERINE | 5 to 20% |
| PETROLATUM | 1 to 10% |
| HYDROGENATED VEGETABLE OIL | 1 to 10% |
| CYCLOPENTASILOXANE | 1 to 10% |
| CAPRYLIC/CAPRIC TRIGLYCERIDE | 1 to 10% |
| SUCROSE DISTEARATE | 1 to 10% |
| DEXTRIN | 1 to 10% |
| *COPERNICIA CERIFERA* CERA | 1 to 5% |
| *HELIANTHUS ANNUUS* SEED OIL UNSAPONIFIABLES | 1 to 5% |
| *PRUNUS DOMESTICA* SEED EXTRACT | 1 to 5% |
| 1,2-HEXANEDIOL | 0.5 to 2% |

PRODUCT 1: Balm-type oil/water (o/w) emulsion

| EU INCI | % INCI |
|---|---|
| SUCROSE STEARATE | 0.5 to 2% |
| CANDELILLA CERA | 0.5 to 2% |
| SQUALANE | 0.5 to 2% |
| GLYCERYL CAPRYLATE | 0 to 2% |
| HYDROXYETHYL ACRYLATE/SODIUM ACRYLOYLDIMETHYL TAURATE COPOLYMER | 0 to 2% |
| XANTHAN GUM | 0 to 2% |
| GLUCOSE | 0 to 2% |
| SORBITOL | 0 to 2% |
| CITRIC ACID | 0 to 2% |
| POLYSORBATE 60 | 0 to 2% |
| SORBITAN STEARATE | 0 to 2% |
| *PERSEA GRATISSIMA* FRUIT EXTRACT/AVOCADO PERSEOSE | 0 to 5% |
| CERAMIDE NP | 0 to 2% |
| PHYTOSPHINGOSINE | 0 to 2% |
| SODIUM HYDROXIDE | 0 to 2% |
| | 100.000000 |

PRODUCT 2: Balm-type O/W emulsion

| EU INCI | % INCI |
|---|---|
| AQUA/WATER/EAU | QS |
| GLYCERINE | 5 to 20% |
| PARAFFINUM LIQUIDUM | 1 to 10% |
| *HELIANTHUS ANNUUS* (SUNFLOWER) SEED OIL | 1 to 10% |
| BEHENYL ALCOHOL | 1 to 10% |
| SUCROSE STEARATE | 1 to 10% |
| CANOLA/CANOLA OIL/RAPESEED OIL | 1 to 10% |
| HYDROXYETHYL ACRYLATE/SODIUM ACRYLOYLDIMETHYL TAURATE COPOLYMER | 1 to 5% |
| PENTYLENE GLYCOL | 0 to 5% |
| BETA-SITOSTEROL | 0.5 to 2% |
| XYLITOL | 0.5 to 2% |
| ZINC GLUCONATE | 0.5 to 2% |
| ACRYLATES/C10-30 ALKYL ACRYLATE CROSSPOLYMER | 0.5 to 2% |
| PALMITAMIDE MEA | 0.5 to 2% |
| 1,2-HEXANEDIOL | 0 to 1% |
| CAPRYLYL GLYCOL | 0 to 1% |
| DISODIUM EDTA | 0 to 1% |
| SODIUM HYDROXIDE | 0 to 1% |
| RHAMNOSE | 0 to 1% |
| SODIUM LAUROYL LACTYLATE | 0 to 1% |
| POLYSORBATE 60 | 0 to 1% |
| SORBITAN ISOSTEARATE | 0 to 1% |
| TOCOPHEROL | 0 to 1% |
| PHYTOSPHINGOSINE | 0 to 1% |
| CERAMIDE NP | 0 to 1% |
| MANNITOL | 0 to 1% |
| ETHYLHEXYLGLYCERIN | 0 to 1% |
| CERAMIDE AP | 0 to 1% |
| CHOLESTEROL | 0 to 1% |
| CARBOMER | 0 to 1% |
| XANTHAN GUM | 0 to 1% |
| CITRIC ACID | 0 to 1% |
| CERAMIDE EOP | 0 to 1% |
| | 100.000000 |

PRODUCT 3: Balm-type O/W emulsion

| EU INCI | % INCI |
|---|---|
| Aqua (Water) | QS |
| *Butyrospermum Parkii* (Shea Butter) | 5 to 20% |
| Glycerine | 1 to 10% |
| Niacinamide | 1 to 10% |
| Cyclohexasiloxane | 1 to 10% |
| Paraffinum Liquidum (Mineral Oil) | 1 to 10% |
| Cetearyl Alcohol | 1 to 10% |
| *Brassica Campestris* (Rapeseed) Seed Oil | 1 to 10% |
| Ammonium Polyacryldimethyltauramide/Ammonium Polyacryloyldimet | 1 to 5% |
| PEG-100 Stearate | 1 to 5% |
| Cera Microcrystallina (Microcrystalline Wax) | 1 to 5% |
| Glyceryl Stearate | 1 to 5% |
| PEG-20 Methyl Glucose Sesquistearate | 1 to 5% |
| Paraffinne | 1 to 5% |
| Sorbitan Tristearate | 1 to 5% |
| Dimethicone | 1 to 5% |
| Dimethiconol | 1 to 5% |
| Disodium EDTA | 0 to 2% |
| Capryloyl Glycine | 0 to 2% |
| Xanthan Gum | 0 to 2% |
| Pentaerythrityl Tetra-di-t-butyl Hydroxyhydrocinnamate | 0 to 2% |
| Preservatives | 0 to 2% |
| | 100.000000 |

PRODUCT 4: Balm-type O/W emulsion

| | |
|---|---|
| Aqua | QS |
| Mineal Oil (Paraffinum Liquidum) | 5 to 20% |
| *Butyrospermum Parkii* (Shea Butter) (*Butyrospermum Parkii* Butter) | 1 to 10% |
| Glycerine | 1 to 10% |
| Polysorbate 60 | 1 to 10% |
| Cetearyl Alcohol | 1 to 10% |
| Dimethicone | 1 to 10% |
| PEG-12 | 1 to 10% |
| *Oenothera Biennis* (Evening Primrose) Oil (*Oenothera Biennis* Oil) | 1 to 5% |
| Butylene Glycol | 1 to 5% |
| Squalane | 1 to 5% |
| Niacinamide | 0.5 to 2% |
| 10-Hydroxydecenoid Acid | 0.5 to 2% |
| *Avena Sativa* (Oat) Leaf/Stem Extract (*Avena Sativa* Leaf/Stem Extract) | 0.5 to 2% |
| BHT | 0 to 2% |
| C 13-14 Isoparaffin | 0 to 2% |
| Cetearyl Glucoside | 0 to 2% |
| Preservatives | 0 to 2% |
| Disodium EDTA | 0 to 2% |
| Laureth-7 | 0 to 2% |
| Maltodextrin | 0 to 2% |
| Polyacrylamide | 0 to 2% |
| Sodium Acetate | 0 to 2% |
| Tocopherol | 0 to 2% |

PRODUCT 5: Balm-type O/W emulsion

| Raw material | % |
|---|---|
| AQUA | QS |
| Geothermal water | 5 to 10% |
| Paraffin oil/synthetic | 1 to 10% |
| Glycerine | 1 to 10% |
| Glyceryl Stearate | 1 to 10% |
| PEG-100 Stearate | 1 to 10% |
| Ketyl alcohol | 1 to 10% |
| Mineral waxes | 1 to 10% |
| Vegetable oil | 1 to 10% |
| Ester | 1 to 10% |
| Polysorbate 20 | 0.5 to 5% |

PRODUCT 5: Balm-type O/W emulsion

| Raw material | % |
|---|---|
| Fragrance | 0.5 to 2% |
| Synthetic gelling agent | 0.5 to 2% |
| pH adjuster | 0 to 2% |
| Antioxidant | 0 to 2% |
| PRESERVATIVES | 0% |
| ACTIVE AGENTS | 0 to 5% |

PRODUCT 6: Balm-type O/W emulsion

| EU INCI | % INCI |
|---|---|
| AQUA/WATER | QS |
| BUTYROSPERMUM PARKII BUTTER/SHEA BUTTER | 5 to 20% |
| GLYCERINE | 1 to 10% |
| DIMETHICONE | 1 to 10% |
| NIACINAMIDE | 1 to 10% |
| PARAFFINUM LIQUIDUM/MINERAL OIL | 1 to 10% |
| CETEARYL ALCOHOL | 1 to 5% |
| BRASSICA CAMPESTRIS OLEIFERA OIL/RAPESEED SEED OIL | 1 to 5% |
| AMMONIUM POLYACRYLDIMETHYLTAURAMIDE/ AMMONIUM POLYACRYLOYLDIMETHYL TAURATE | 1 to 5% |
| PEG-100 STEARATE | 1 to 5% |
| GLYCERYL STEARATE | 1 to 5% |
| PEG-20 METHYL GLUCOSE SESQUISTEARATE | 1 to 5% |
| CERA MICROCRYSTALLINA/MICROCRYSTALLINE WAX | 1 to 5% |
| PARAFFIN | 1 to 5% |
| SORBITAN TRISTEARATE | 0.5 to 2% |
| MANNOSE | 0 to 2% |
| DISODIUM EDTA | 0 to 1% |
| CAPRYLOYL GLYCINE | 0 to 1% |
| VITREOSCILLA FERMENT | 0 to 1% |
| XANTHAN GUM | 0 to 1% |
| PENTAERYTHRITYL TETRA-DI-T-BUTYL HYDROXYHYDROCINNAMATE | 0 to 1% |
| PRESERVATIVES | 0 to 2% |
| | 100.000000 |

PRODUCT 7: O/W atopy milk

| EU INCI | % INCI |
|---|---|
| AQUA | QS |
| PROPANEDIOL DICAPRYLATE | 5 to 20% |
| CAPRYLIC/CAPRIC TRIGLYCERIDE | 1 to 10% |
| C10-18 TRIGLYCERIDES | 1 to 10% |
| GLYCERINE | 1 to 10% |
| BUTYROSPERMUM PARKII | 1 to 10% |
| EMULSIFIER | 1 to 10% |
| 1,2-HEXANEDIOL | 1 to 10% |
| ACTIVE AGENT | 0 to 5% |
| HYDROXYETHYL ACRYLATE/SODIUM ACRYLOYLDIMETHYL TAURATE COPOLYMER | 0 to 2% |
| JOJOBA ESTERS | 0 to 2% |
| CAPRYLYL GLYCOL | 0 to 2% |
| CETYL ALCOHOL | 0 to 2% |
| CITRIC ACID | 0 to 2% |
| TOCOPHERYL ACETATE | 0 to 2% |
| CO-EMULSIFIER | 0 to 2% |

PRODUCT 8: Emollient cream-type O/W emulsion

| EU INCI | % INCI |
|---|---|
| AQUA | QS |
| GLYCERINE | 5 to 20% |
| PETROLATUM | 1 to 10% |
| HYDROGENATED VEGETABLE OIL | 1 to 10% |
| CYCLOPENTASILOXANE | 1 to 10% |
| CAPRYLIC/CAPRIC TRIGLYCERIDE | 1 to 10% |
| SUCROSE DISTEARATE | 1 to 10% |
| DEXTRIN | 1 to 10% |
| HELIANTHUS ANNUUS SEED OIL UNSAPONIFIABLES | 1 to 5% |
| PRUNUS DOMESTICA SEED EXTRACT | 1 to 5% |
| 1,2-HEXANEDIOL | 0.5 to 2% |
| SUCROSE STEARATE | 0.5 to 2% |
| CANDELILLA CERA | 0.5 to 2% |
| SQUALANE | 0.5 to 2% |
| GLYCERYL CAPRYLATE | 0 to 2% |
| XANTHAN GUM | 0 to 2% |
| GLUCOSE | 0 to 2% |
| SORBITOL | 0 to 2% |
| CITRIC ACID | 0 to 2% |
| PERSEA GRATISSIMA FRUIT EXTRACT | 0 to 2% |
| CERAMIDE NP | 0 to 2% |
| PHYTOSPHINGOSINE | 0 to 2% |
| | 100.000000 |

According to another preferred embodiment, the reference expression level of a biological marker is the expression level of said marker obtained in a skin model obtained from a skin sample from a child, said model not having been treated with the formulation or active agent of interest, and not having been exposed to conditions leading to atopic dermatitis according to at least one of the tests A, B, C and D.

According to another preferred embodiment, the reference expression level of a biological marker is the expression level of said marker obtained in a skin model obtained from a skin sample from a child, said model not having been treated with the formulation or active agent of interest, but having been exposed to conditions leading to atopic dermatitis according to at least one of the tests A, B, C and D.

According to another preferred embodiment, the reference expression level of a biological marker is the expression level of said marker obtained in a skin model obtained from a skin sample from a child, said model not having been treated with the formulation or active agent of interest, but having been exposed to conditions leading to atopic dermatitis according to at least one of the tests A, B, C and D.

According to another embodiment, the reference expression level of a biological marker is the expression level of said marker obtained in a skin model obtained from a skin sample from a child, treated with the formulation or active agent of interest, and not having been exposed to conditions leading to atopic dermatitis according to at least one of the tests A, B, C and D.

The skilled person will also easily understand that the comparison of step e) of test A, of step e) of test B, of step g) of test C or of step f) of test D is preferably made between expression level measurements obtained for skin models obtained from skin samples from children, of similar or even identical histological structures. For the purposes of the present application, "similar histological structures" means that the relative proportions of the cell types included in the compared skin models are similar. Thus, it is preferable that the relative proportions of the cell types included in the skin model of step a) of each of these tests do not differ by more than 5% from the relative proportions of the cell types included in the skin model used to obtain the reference expression level of step e) of test A, of step e) of test B, of step g) of test C or of step f) of test D. For the purposes of the present application, "relative proportion of a cell type" means the ratio of the number of cells corresponding to that cell type to the total number of cells included in the skin model. Thus, for example, it is preferable that the proportion of keratinocytes relative to the total number of cells in the skin model of step a) of each of these tests does not differ by more than 5% from the proportion of keratinocytes on the total number of cells in the skin model used to obtain the reference expression level of step e) of test A, of step e) of test B, of step g) of test C or of step f) of test D. For the purposes of the present application, "identical histological structures" means that the relative proportions of the cell types included in the compared skin models are identical. For the purposes of the present invention, the relative proportions of the cell types included in the nipple skin model of step a) of each of these tests are identical to the relative proportions of the cell types included in the skin model used to obtain the reference expression level of step e) of test A, of step e) of test B, of step g) of test C or of step f) of test D when they differ by no more than 0.1%. Advantageously, the proportion of keratinocytes relative to the total number of cells in the skin model of step a) of each of these tests does not differ by more than 0.1% from the proportion of keratinocytes relative to the total number of cells in the skin model used to obtain the reference expression level of step e) of test A, of step e) of test B, of step g) of test C or of step f) of test D.

The skilled person will just as easily understand that the comparison of step e) of test A, of step e) of test B, of step g) of test C or of step f) of test D is preferably made between expression level measurements obtained for skin models that are of similar or even identical height, volume or weight. Thus, it is preferable that the size, volume, or weight of the skin model of step a) of each of these tests should not differ by more than 5% from the size, volume, or weight of the skin model used to obtain the reference expression level of step e) of test A, of step e) of test B, of step g) of test C or of step f) of test D. More preferentially, the size, volume and weight of the skin model of step a) of each of these tests will not differ by more than 5% from the size, volume and weight of the skin model used to obtain the reference expression level of step e) of test A, of step e) of test B, of step g) of test C or of step f) of test D. Even more preferentially, the size, volume and weight of the skin model of step a) of each of these tests will not differ by more than 0.1% from the size, volume and weight of the skin model used to obtain the reference expression level of step e) of test A, of step e) of test B, of step g) of test C or of step f) of test D.

Alternatively, if the skin models differ by more than 5% in height, volume and weight, the skilled person may normalize the level obtained in step c) and the reference level of step e) of test A, of step e) of test B, of step g) of test C or of step f) of test D.

This normalization factor may for example be a directly accessible physical marker such as the mass of cells in the sample, or the mass of a cellular component such as the mass of cellular DNA or the mass of cellular proteins.

It may also be advantageous to use as normalization factor the expression level of a gene that is expressed at the same level in all, or almost all, cells of the body. In other words, according to a particular embodiment of the present invention, the expression level of a housekeeping gene is used as normalization factor. According to another embodiment, the level obtained in step d) of test A, in step d) of test B, in step f) of test C or in step e) of test D, and the reference level are normalized using the expression level, not of housekeeping genes, but of proteins encoded by said genes. A housekeeping gene is a gene expressed in all cell types, which encodes a protein having a basic function necessary for the survival of all cell types. A list of human housekeeping genes can be found in Eisenberg et al. (*Trends in Genet*, 19: 362-365, 2003). The housekeeping genes according to the invention include for example the RPS28, GAPDH, B2M, TFRC, YWHAZ, RPLO, 18S, GUSB, UBC, TBP, GAPDH, PPIA, POLR2A, ACTB, PGK1, HPRT1, IP08 and HMBS genes. Preferably, the housekeeping gene is the RPS28 gene (gene ID: 6234; NM_001031) which encodes ribosomal protein S28 (NP_001022.1) or the GAPDH gene (NCBI reference: Gene ID: 2597), with sequence NM_002046, which encodes glyceraldehyde 3-phosphate dehydrogenase (NP_002037.2).

The skilled person will therefore easily be able to evaluate the efficacy of the formulation of interest based on a comparison of step e) of test A, of step e) of test B, of step g) of test C or of step f) of test D.

According to another aspect, the invention relates to a kit for implementing a method according to the invention, comprising the means necessary for measuring the expression level of at least one marker selected from markers of activities that inhibit bacterial physiology, markers of immunity, markers of inflammation, markers of the barrier function and markers preferentially expressed in stem cells. Preferably, the markers present in the kit of the invention are those described above.

According to a particular embodiment, the kit according to the invention further comprises the means necessary for measuring the expression level of a combination of biological markers selected from the group comprising or consisting of:

at least one inflammation marker and at least one barrier marker as defined above; or at least one inflammation marker and at least one marker preferentially expressed in stem cells, as defined above; or at least one barrier marker and at least one marker preferentially expressed in stem cells, as defined above.

In a more preferential embodiment, said combination comprises at least one inflammation marker and at least one barrier marker and at least one marker preferentially expressed in stem cells, as defined above.

The following examples are provided here by way of illustration and are not, unless otherwise indicated, intended to be limiting.

FIGURE LEGENDS

FIG. 1: Effect of product P8 on *S. aureus* biofilm formation on the surface of epidermises, observed after 6 h by scanning electron microscopy. A: Untreated control; Magnification ×750. B: Untreated control; Magnification ×10000. C: Product P8; Magnification ×750.

Figure 2:
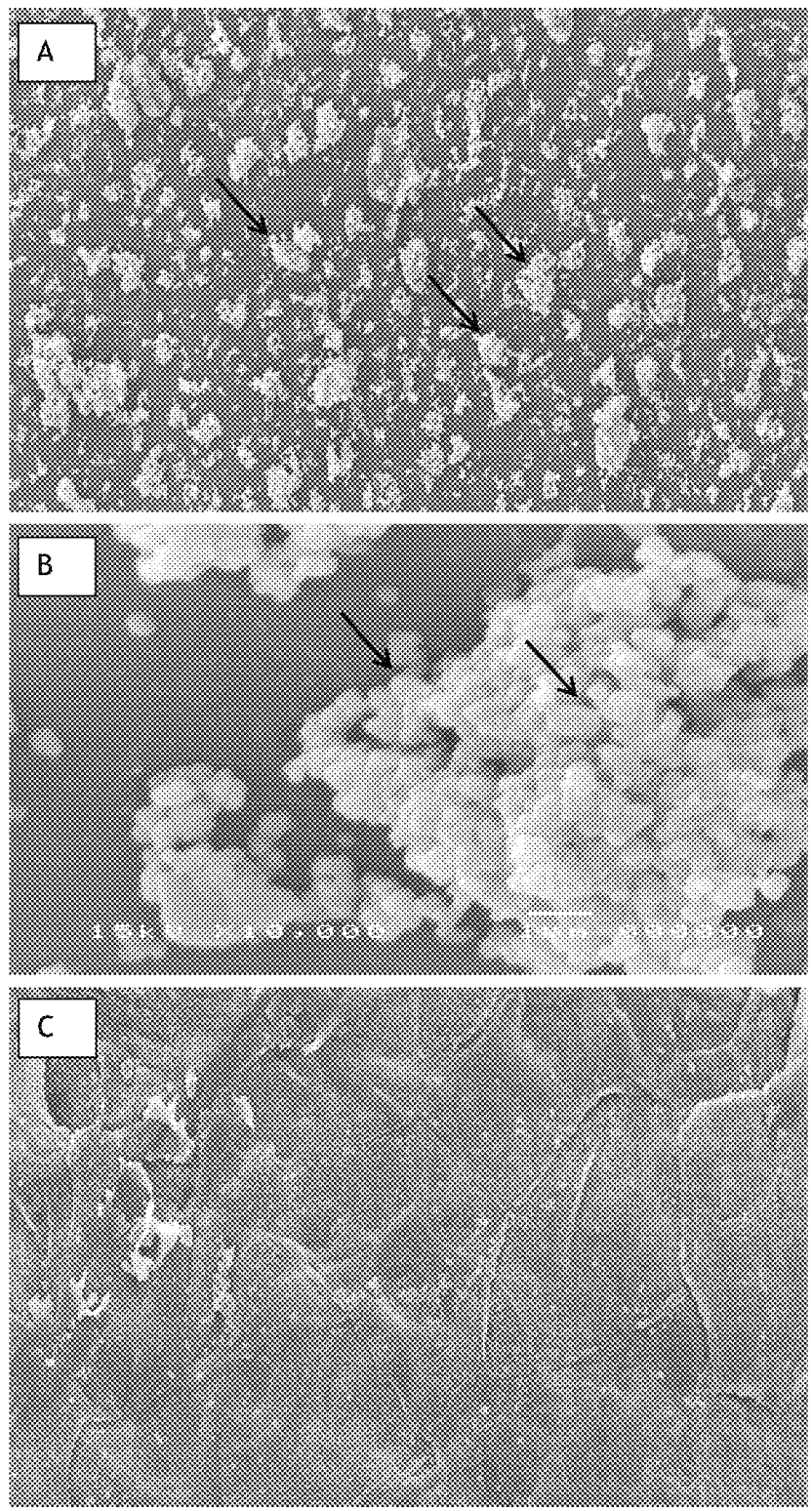
Figure 2:
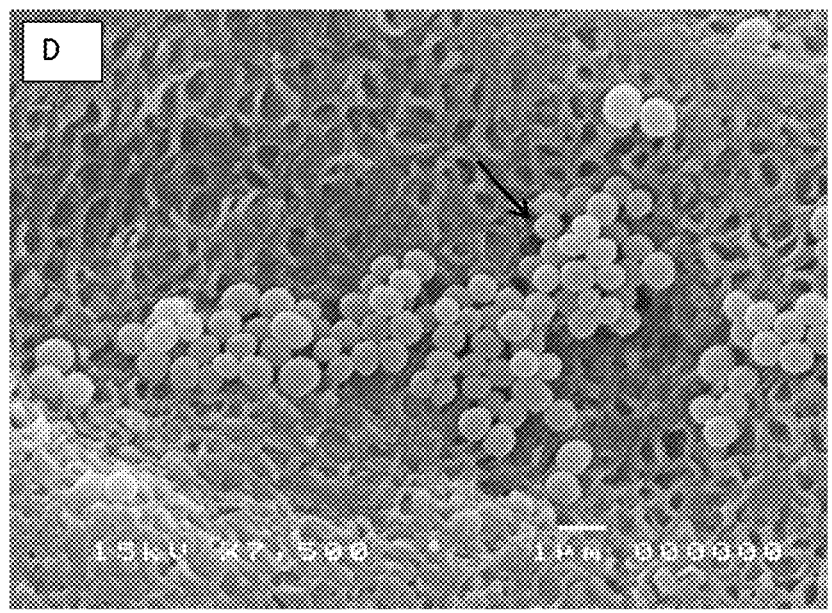

FIG. 2: Effect of product P8 on *S. aureus* biofilm formation on the surface of epidermises, observed after 24 h by scanning electron microscopy. A: Untreated control; Magnification ×750. B: Untreated control; Magnification ×10000. C: Product P8; Magnification ×750. D: Product P8; Magnification ×10000.

Figure 3:
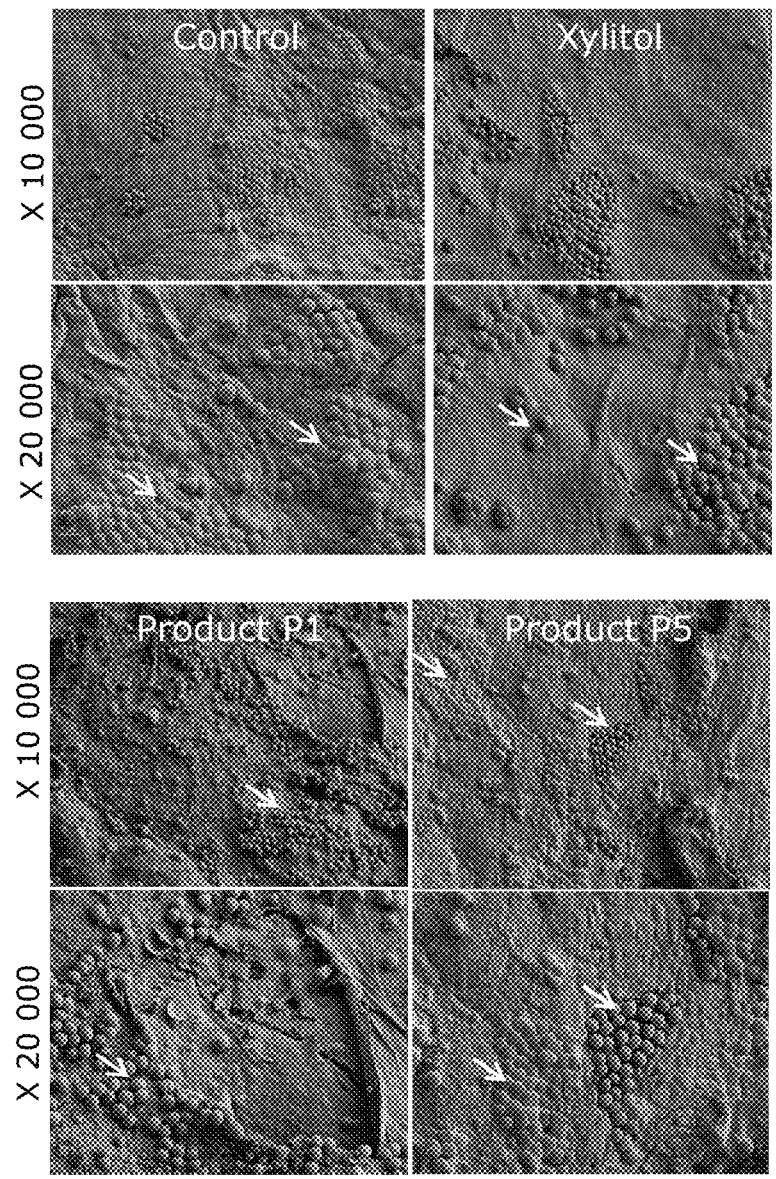

FIG. 3: Effect of products P1 and P5 and of Xylitol on *S. aureus* biofilm formation on the surface of epidermises, observed after 24 h by scanning electron microscopy at magnification ×10000 (A) or ×20000 (B).

EXAMPLES

I. Model of TH2 Inflammation

The biological efficacy of 6 products (P1, P2, P3, P4, P5 and P8: see Products 1 to 5 and 8 above) was evaluated in a model of atopic dermatitis induced by a mix of Th2 cytokines on 6-month-old epidermises.

A. Materials and Methods

Reconstructed epidermises were made with keratinocytes from a 6-month-old donor.

The epidermises were reconstructed according to the model derived from the method of Poumay et al. (*Arch Dermatol Res* 2004; 296: 203-11). The epidermises were treated or not (control) topically with the test products at a rate of 5 mg/cm$^2$. After a 24-hour pre-incubation, the epidermises were again treated with the products at a rate of 2 mg/cm$^2$ and optionally stimulated with the mixture of Th2 cytokines IL4/IL13/IL22/TNFα at 3 ng/ml.

After 24 hours of incubation, gene expression of the barrier function, stem cell and inflammation markers listed in Table 1 was evaluated by qRT-PCR (quantitative real-time PCR).

TABLE 1

Classification and name of the genes studied

| Cluster name | Abbreviation | Gene name |
|---|---|---|
| Housekeeping | RPS28 | Ribosomal protein 28S |
| | GADPH | Glyceraldehyde-3-phosphate dehydrogenase |
| Stem cells | ITGB1 | Integrin beta 1 |
| | KRT15 | Keratin15 |
| | KRT19 | Keratin 19 |
| | BIRC5 | Baculoviral IAP repeat-containing 5 (survivin) |
| | NOTCH1 | Notch homolog 1 |
| Epidermal differentiation, Barrier function, Moisturizing | FLG | Filaggrine |
| | KRT1 | Keratin 1 |
| | KRT10 | Keratin 10 |
| | SCEL | Sciellin |
| | BARX2 | Barx homeobox 2 |
| | LOR | Loricrin |
| | IVL | Involucrin |
| | TGM1 | Transglutaminase 1 |
| | DSG1 | Desmoglein 1 |
| | CDSN | Corneodesmosin |
| | CLDN1 | Claudin 1 |
| | CASP14 | Caspase 14 |
| | SMPD1 | Sphingomyelinase |
| | GBA | Glucocerebrosidase |
| | LASS6 | Ceramide synthase |
| Inflammation | CCL2 | Chemokine (C-C motif) ligand 2 or monocyte chemoattractant protein 1 (MCP1) |
| | CXCL1 | C—X—C motif chemokine ligand 1 |
| | CCL7 | Chemokine (C-C motif) ligand 7 or monocyte-specific chemokine 3 (MCP3) |

After 48 hours of incubation, the amounts of natural moisturizing factors (NMFs) and ceramides produced by the epidermises were evaluated:

Analysis of Ceramides:

Epidermal lipids were extracted by stirring the epidermises from a mixture of organic solvents for 2 hours at room temperature. A solid/liquid extraction treatment was then carried out to isolate ceramides from the other lipids making up the epidermises.

The presence of ceramides with a sphingosine [S], dihydrosphingosine [DS] and phytosphingosine [P] sphingoid base with an even chain length ranging from 16 to 22 carbon atoms was investigated by an LC/MS method.

The ceramide content was normalized to the amount of total protein (BCA assay).

Analysis of NMF Elements:

The reconstructed epidermises were extracted under stirring for 2 h at room temperature from an aqueous mixture in the presence of a non-ionic surfactant to promote extraction of the markers of interest.

Filaggrin catabolites were measured by an LC/UV method to screen urocanic acid (UCA) under its two isomers (cis and trans) and L-pyrrolidone carboxylic acid (PCA).

The NMF content was normalized to the amount of total protein (BCA assay).

B. Results

1. Analysis of Barrier Marker Gene Expression

The deficit of barrier function is one of the key parameters of atopic dermatitis pathophysiology. We evaluated the expression level of different markers of keratinocyte differentiation and of epidermal barrier function in the model of infant epidermises subjected to Th2 stress.

Incubation of 6-month-old reconstructed epidermises in the presence of the Th2 cytokine mixture led to a strong inhibition of all the barrier markers studied (on average, 61% inhibition; Table 2).

This is in correlation with the data in the literature and validates the model as mimicking the barrier function impairment induced by the Th2 inflammatory environment in the context of atopic dermatitis pathophysiology.

TABLE 2

Gene expression level of barrier markers in 6-month-old epidermises treated with the Th2 cytokine mix
Relative expression in % in relation to the Control

| | 6-month-old control epidermises | 6-month-old Th2 epidermises |
|---|---|---|
| FLG | 100 | 11 |
| KRT1 | 100 | 25 |
| KRT10 | 100 | 26 |
| SCEL | 100 | 29 |
| BARX2 | 100 | 36 |
| LOR | 100 | 25 |
| IVL | 100 | 31 |
| DSG1 | 100 | 30 |
| CDSN | 100 | 79 |
| CLDN1 | 100 | 63 |
| CASP14 | 100 | 26 |
| SMPD1 | 100 | 40 |
| GBA | 100 | 81 |
| LASS6 | 100 | 40 |
| Mean expression of barrier markers (%) | 100 | 39 |

Filaggrin (FLG), keratins 1 and 10 (KRT1, KRT10) and BARX2 are markers of epidermal differentiation. On the other hand, filaggrin, a precursor of NMFs, is a key marker involved in atopic dermatitis pathophysiology.
Loricrin (LOR) and involucrin (IVL) are constitutive proteins of the corneal envelope.
Sciellin (SCL) is a precursor of the corneal envelope.
Desmoglein 1 (DSG1) and corneodesmosin (CDSN) are constitutive proteins of corneodesmosomes which ensure corneocyte cohesiveness within the corneal layer.
Claudin 1 (CLDN1) is a constitutive protein of the tight junctions that play a role in the barrier function of the epidermis and are described as a second barrier against water loss after the stratum corneum.
Caspase 14 (CASP14) is an enzyme involved in processing filaggrin to produce NMF.
Sphingomyelinase (SMPD1), glucocerebrosidase (GBA) and ceramide synthase (LASS6) are enzymes involved in the synthesis of epidermal lipids, notably ceramides, which are key to ensuring barrier watertightness.

The tested products induced an increase in gene expression of key barrier markers in 6-month-old epidermises incubated under Th2 stress conditions (Table 3).

The efficacy of the products on barrier marker expression can be classified as follows: P1>P5>P3>P2>P4.

TABLE 3

Gene expression level of barrier markers in 6-month-old epidermises treated with the Th2 cytokine mix - Product effect
Relative expression in % compared with the Th2 Control

|     | Claudin 1 | SMPD1 | Involucrin | TGM | Average |
| --- | --- | --- | --- | --- | --- |
| Th2 | 100 | 100 | 100 | 100 | 100 |
| P1 | 639 | 346 | 1484 | 916 | 846 |
| P2 | 180 | 105 | 210 | 142 | 159 |
| P3 | 141 | 171 | 107 | 233 | 163 |
| P4 | 115 | 76 | 144 | 96 | 108 |
| P5 | 555 | 221 | 1767 | 635 | 795 |

2. Analysis of Inflammation Marker Gene Expression

Incubation of 6-month-old epidermises in the presence of the Th2 cytokine mixture induced a significant overexpression of chemokines CXCL1 (Chemokine ligand 1), CCL2 (Chemokine ligand 2) and CCL7 (Chemokine ligand 7) (Table 4).

These chemokines, responsible for recruiting inflammation cells in the skin, play an important role in amplifying the inflammatory response in the context of atopic dermatitis. In particular, chemokines CXCL1 and CCL2 have been described as being overexpressed in atopic skin. Thus, this model represents the amplification of the inflammatory response related to the Th2 environment in atopic dermatitis.

Topical application of the test products modulated the overexpression of chemokines induced by Th2 stress, and the efficacy of the products can be classified as follows: P5≥1>P2>P3=P4.

TABLE 4

Gene expression level of inflammation markers in 6-month-old epidermises treated with the Th2 cytokine mix - Product effect
Relative expression in % in relation to the Control

|  | CCL2 | | CXCL1 | | CCL7 | |
| --- | --- | --- | --- | --- | --- | --- |
|  | Expression level | % Inhibition | Expression level | % Inhibition | Expression level | % Inhibition |
| 6-month-old control epidermises | 100 | | 100 | | 100 | |
| 6-month-old Th2 epidermises | 9863 | | 3688 | | 2583 | |
| P1 | 99 | −99% | 2250 | −39% | 103 | −96% |
| P2 | 4636 | −53% | 1549 | −58% | 1653 | −36% |
| P3 | 3255 | −67% | 3688 | 0 | 1343 | −48% |
| P4 | 3057 | −69% | 3835 | +4% | 1188 | −54% |
| P5 | 0 | −100% | 996 | −73% | 129 | −95% |

CXCL1 (Chemokine ligand 1): Chemoattractant for neutrophils, overexpressed in atopic dermatitis.

CCL2 or MCP1 (Chemokine ligand 2): Chemoattractant for monocytes and basophils; overexpressed in atopic dermatitis, where it is responsible for recruiting dendritic cell precursors.

CCL7 or MCP3 (Chemokine ligand 7): Chemoattractant for monocytes/macrophages.

3. Analysis of Stem Cell Marker Gene Expression

Tissue stem cells in permanent renewal are traditionally defined as rare and relatively quiescent cells. They have a unique capacity for self-renewal and tissue regeneration that allows them to ensure the homeostasis and integrity of the tissue in which they reside.

Among epidermal stem cells, interfollicular stem cells located in the basal layer constitute the main epidermal reservoir of stem cells. These cells reside in an anatomical and functional microenvironment, the niche, which helps to maintain their characteristics, especially when physiological conditions change. Interfollicular stem cells and their niches are involved in maintaining the integrity and regeneration of the epidermis. Stem cells can be identified only by following several markers. We have thus evaluated the expression level of different gene markers characteristic of stem cells in the model of Th2 inflammation.

Incubation of 6-month-old epidermises in the presence of the Th2 cytokine mixture induced a significant decrease (−39%) in the mean expression level of the stem cell marker pool studied (Table 5).

This is, to our knowledge, the first time that an effect of Th2 inflammation has been observed on stem cell markers. These observations tend to confirm the high vulnerability of the cell stock in infant epidermis to external insult modelled here by Th2 stress typical of atopic dermatitis pathogenesis.

TABLE 5

Gene expression level of stem cell markers in 6-month-old epidermises treated with the Th2 cytokine mix
Relative expression in % in relation to the Control

|  | 6-month-old control epidermises | 6-month-old Th2 epidermises |
| --- | --- | --- |
| ITGB1 | 100 | 49 |
| KRT15 | 100 | 86 |
| KRT19 | 100 | 89 |
| BIRC5 (SURVIVIN) | 100 | 47 |

TABLE 5-continued

Gene expression level of stem cell markers in 6-month-old epidermises treated with the Th2 cytokine mix
Relative expression in % in relation to the Control

|  | 6-month-old control epidermises | 6-month-old Th2 epidermises |
| --- | --- | --- |
| NOTCH1 | 100 | 35 |
| Mean expression of the stem cell marker pool (%) | 100 | 61 |

The application of product P1, and more moderately of product P5, restored the expression level of the stem cell marker pool to a level identical to that of the untreated control (Table 6). Products P2, P3 and P4 did not show any protective efficacy of the stem cell marker pool.

TABLE 6

Gene expression level of the stem cell marker pool in 6-month-old epidermises treated with the Th2 cytokine mix - Product effect
Relative expression in % in relation to the Control

|  | ITGB1 | KRT15 | KRT19 | BIRC5 | TP63 | NOTCH1 | Marker pool average |
|---|---|---|---|---|---|---|---|
| Control | 100 | 100 | 100 | 100 | 100 | 100 | 100 |
| Th2 | 49 | 86 | 89 | 47 | 91 | 35 | 66 |
| P1 | 141 | 34 | 185 | 43 | 48 | 157 | 101 |
| P2 | 61 | 29 | 105 | 22 | 109 | 54 | 63 |
| P3 | 53 | 55 | 56 | 10 | 56 | 47 | 46 |
| P4 | 57 | 15 | 91 | 39 | 65 | 37 | 51 |
| P5 | 86 | 23 | 230 | 58 | 51 | 109 | 93 |

4. Analysis of NMF and Ceramide Amounts

Incubation of 6-month-old epidermises in the presence of the Th2 cytokine mixture resulted in a significant decrease in the amount of NMFs (−52%, p<0.001) and ceramides (−41%, p<0.001; Tables 7 and 8, respectively).

This is in correlation with the data in the literature and confirms the validity of the model to mimic the impairment of barrier function and of mechanisms of hydration regulation induced by the Th2 inflammatory environment in the context of atopic dermatitis pathophysiology.

Under these Th2 stress conditions, products P1 and P8 induce a significant increase in the production of NMFs and ceramides by the reconstructed epidermises, with a greater effect of product P1 (Tables 7 and 8).

TABLE 7

Quantification of NMF content in 6-month-old reconstructed epidermises under Th2 stress conditions - Statistics: One-way analysis of variance followed by Tukey's test

|  | NMF ($\Sigma$ UCA and PCA in µg/mg protein) (mean ± standard deviation) | Change (%) |
|---|---|---|
| 6-month-old control epidermises | 22.65 ± 1.878 |  |
| 6-month-old Th2 epidermises | 10.84 ± 1.005 | −52% p < 0.001 |
| P1 | 16.5 ± 1.718 | +52% p < 0.001 |
| P8 | 12.88 ± 0.582 | +19% p < 0.05 |

TABLE 8

Quantification of ceramide content in 6-month-old reconstructed epidermises under Th2 stress conditions - Statistics: One-way analysis of variance followed by Tukey's test

|  | Ceramides (AU/mg protein) (mean ± standard deviation) | Change (%) |
|---|---|---|
| 6-month-old control epidermises | 148.4 ± 8.045 |  |
| 6-month-old Th2 epidermises | 88.27 ± 7.125 | −41% p < 0.001 |
| P1 | 110.7 ± 7.322 | +25% p < 0.05 |
| P8 | 100.6 ± 8.985 | +14% p < 0.1 |

C. Conclusion

Treatment of reconstructed epidermises with a mixture of Th2 cytokines reproduces the pathophysiological characteristics of atopic dermatitis related to the Th2 inflammatory environment: impairment of the skin barrier, amplification of local inflammation.

Applied to epidermises obtained from keratinocytes from a 6-month-old donor, this model is, to our knowledge, the first baby-specific model mimicking the inflammatory environment of atopic dermatitis.

Furthermore, this model demonstrated, for the first time, the possible impairment of the stem cell stock by the Th2 inflammatory environment.

This model also allows a comparative study of the biological activity of topical products on the protection of barrier and stem cell markers as well as on modulation of the inflammatory response.

II. Model of Initiation of Atopic Dermatitis

The biological efficacy of 4 products (P1, P4, P5, P6) was evaluated in a model reproducing the initiation phase of atopic dermatitis on reconstructed epidermises, from a 6-month-old donor, stimulated by a Poly (I:C)+IL1α mixture.

Poly I:C is a TLR3 agonist, IL1α is a pro-inflammatory cytokine. The stress induced by this mixture of molecules mimics the cascade of reactions induced by bacterial attack and leading to the induction of a Th2 inflammatory response. It is therefore a model that reproduces the initiation of an inflammatory response characteristic of atopic dermatitis.

A. Materials and Methods

Reconstructed epidermises were made, as described above, with keratinocytes from a 6-month-old donor. The epidermises were optionally treated topically (at a rate of 5 mg/cm$^2$) with the test products and pre-incubated for 24 h. The epidermises were again optionally treated topically (at a rate of 2 mg/cm$^2$) with the products and optionally stimulated with the mixture of inducers: 10 µg/ml Poly(I:C)+10 ng/ml IL1α.

After 4 h of incubation, gene expression of the inflammatory markers was evaluated by qRT-PCR (quantitative real-time PCR) with n=2.

Table 9 lists the genes that were studied.

TABLE 9

Classification and name of the genes studied

| Cluster name | Abbreviation | Gene name |
|---|---|---|
| Housekeeping | RPS28 | Ribosomal protein 28S |
|  | GADPH | Glyceraldehyde-3-phosphate dehydrogenase |
| Inflammation/ Pruritus | IL6 | Interleukin 6 |
|  | IL18 | Interleukin 18 |
|  | CCL3 | Chemokine (C-C motif) ligand 3 or macrophage inflammatory protein 1alpha (MIP1α) |
|  | CCL5 | Chemokine (C-C motif) ligand 5 or regulated on activation, normal T cell expressed and secreted (RANTES) |
|  | CCL7 | Chemokine (C-C motif) ligand 7 or monocyte-specific chemokine 3 (MCP3) |
|  | KLK5 | Kallikrein 5 or stratum corneum trypsin-like enzyme (SCTE) |

B. Results: Analysis of Inflammation and Pruritus Marker Gene Expression

Stimulation of 6-month-old epidermises by Poly(I:C)-+IL1α stress induced a very high overexpression of chemokines CCL3, CCL5 and CCL7, involved in the recruitment and activation of inflammatory cells (Table 10). In particular, chemokines CCL3 (or MIP1α) and CCL5 (or RANTES) are described as being overexpressed in atopic skin and responsible for the activation and recruitment of Th2 cells. Thus, this model effectively mimics the initiation phase of the inflammatory cascade leading to establishment of the Th2 inflammatory environment specific to atopic dermatitis.

Furthermore, Poly(I:C)-FIL1α stress also induced overexpression of kallikrein 5. This protease, whose activity is increased in atopic dermatitis, plays a role in controlling desquamation, inflammation and pruritus (via PAR2 activation), thus contributing to atopic dermatitis pathogenesis related to barrier impairment and induction of inflammation and pruritus.

The various products tested resulted in a more or less marked decrease in the gene expression of markers of inflammation and pruritus; the activity potential of the products can be classified as follows: P1>P5>P4P6. Only product P1 showed inhibitory efficacy on all markers studied.

TABLE 10

Gene expression level of inflammation and pruritus markers Relative expression in %.

|  | IL6 | IL18 | CCL3 | CCL5 | CCL7 | KLK5 |
| --- | --- | --- | --- | --- | --- | --- |
| Control | nd | nd | 100 | 100 | 100 | 100 |
| PolyI:C + IL1 | 100 | 100 | 5532 | 9280 | 8462 | 136 |
| P1 | 12 | 54 | 664 | 3248 | 508 | 95 |
| P4 | 246 | 95 | 2213 | 9373 | 6770 | 140 |
| P5 | 188 | 65 | 2600 | 7610 | 4400 | 167 |
| P6 | 114 | 138 | 3872 | 12806 | 6600 | 155 |

IL6 (Interleukin 6): pro-inflammatory cytokine
IL18 (Interleukin 18): cytokine overexpressed in atopic skin, involved in induction of the Th2 response
CCL3 or MIP1α (Chemokine ligand 3): Chemoattractant for inflammatory cells; overexpressed in atopic dermatitis.
CCL5 or RANTES (Chemokine ligand 5): Chemoattractant for inflammatory cells; overexpressed in atopic dermatitis.
CCL7 or MCP3 (Chemokine ligand 7): Chemoattractant for monocytes/macrophages.
KLK5 or SCTE (Kallikrein 5): protease overexpressed in atopic dermatitis, involved in desquamation, inflammation and pruritus.

C. Conclusion

Treatment of 6-month-old epidermises with the poly(I:C)/IL1α mixture effectively models the induction phase of the Th2 response in atopic dermatitis. Indeed, this stress led to an overexpression of chemokines and molecular messengers involved in the recruitment and activation of Th2 cells.

This model of initiation of the inflammatory phase of atopic dermatitis made it possible to evaluate and classify the biological efficacy of different topical products on the markers of inflammation and pruritus.

III. Model of Response to *Staphylococcus aureus* on Immunocompetent Epidermises The biological efficacy of products P1 and P5 was evaluated in a model mimicking *S. aureus*-induced atopic dermatitis in reconstructed 1-year-old epidermises made immunocompetent by co-culture with immune cells (THP1 monocyte cell line). Co-culture with the immune cells made it possible to establish an adaptive and protective response to *S. aureus* immune-mediated by induction of a Th2-type response.

A. Materials and Methods

Reconstructed epidermises obtained with keratinocytes from a one-year-old donor were infected with a methicillin-resistant *S. aureus* strain (MRSA; ATCC 33591) at a rate of $2 \cdot 10^6$ cfu/epidermis for 4 hours, after undergoing slight surface abrasion. Non-adherent bacteria were then removed by rinsing and the epidermises were placed in co-culture with THP1 cells ($10^5$ cells/ml). At the same time, the test products were applied to the surface of the epidermises (20 µl/epidermis). After 16 h of co-culture (T1), the gene expression of different markers was evaluated by qRT-PCR (quantitative real-time PCR) with n=3.

On a second series of epidermises, the products were reapplied and the epidermises incubated for 24 h in the absence of THP1 cells. At the end of this incubation period, the gene expression of different markers was evaluated by qRT-PCR (quantitative real-time PCR) with n=3 (T2).

Table 11 lists the genes that were studied.

TABLE 11

Classification and name of the genes studied

| Cluster name | Abbreviation | Gene name |
| --- | --- | --- |
| Housekeeping | GADPH | Glyceraldehyde-3-phosphate dehydrogenase |
| Innate immunity | HBD2 | Human beta-defensin 2 |
|  | TLR2 | Toll-like receptor 2 |
| TH2 inflammation | TSLP | Thymic stromal lymphopoietin |
| Barrier/Pruritus | KLK5 | Kallikrein 5 or stratum corneum trypsin-like enzyme (SCTE) |
| Barrier | CLDN1 | Claudin-1 |
| Stem cells | K19 | Keratin 19 |
|  | ITGA6 | Integrin alpha 6 |
|  | ITGB1 | Integrin beta 1 |

B. Results

1. Evaluation of the Epidermal Response

T1: Atopic Dermatitis Induction Phase

After 16 hours of co-culture (T1) with immune cells, analysis of gene expression in the 1-year-old epidermises showed overexpression of kallikrein-5, β-defensin 2 and TSLP, as well as a decrease in TLR2 (Table 12).

Stimulation of kallikrein-5 would indicate an early epidermal response in favour of induction of the Th2 inflammatory phase (via TSLP), impairment of the barrier, and pruritus.

TSLP itself is moderately increased, indicating the beginning of induction of Th2 inflammation.

Stimulation of β-defensin 2, an anti-microbial peptide impaired in atopic dermatitis, shows that in this early phase, the epidermis sets up defence mechanisms to prevent colonization by *S. aureus*.

TLR2, a receptor involved in pathogen recognition and induction of the immune response, whose expression is decreased in atopic dermatitis, is decreased in the model, which tends to show the inability of the skin to defend itself, with a deficit of this important element of innate immunity.

Thus, in this early induction phase of the model, molecular signals related to the immune response appear to be in place to induce the Th2 shift characteristic of atopic dermatitis.

TABLE 12

Gene expression level of markers in the model of "immunocompetent" epidermises colonized by S. aureus
(T1, Early phase, 16 h post-colonization)

|  | KLK5 | hBD2 | TLR2 | TSLP |
|---|---|---|---|---|
| Control | 1 | 1 | 1 | 1 |
| S. aureus + THP1 | 1.425 | 1.469 | 0.308 | 1.299 |

T2: Phase Modelling Established Atopic Dermatitis

After 16 hours of co-culture then 24 hours of incubation, the response of the epidermises to colonization by S. aureus reproduces the main characteristics of atopic dermatitis pathophysiology (Table 13):

Barrier impairment, represented by inhibition of claudin-1, the constitutive protein of tight junctions;

Inhibition of defence mechanisms related to innate immunity: hBD2 and TLR2;

Overexpression of TSLP, key cytokine in atopic dermatitis pathophysiology, involved in induction of a Th2 inflammatory response.

In addition, a marked decrease in stem cell markers (Keratin 19, Integrins α6 and β1) was observed, comparable to the results obtained in the Th2 model described above.

TABLE 13

Gene expression level of markers in the model of "immunocompetent" epidermises colonized by S. aureus
(T2, Late phase, 16 + 24 h post-colonization)

|  | CLDN1 | KRT19 | ITGA6 | ITGB1 | hBD2 | TLR2 | TSLP |
|---|---|---|---|---|---|---|---|
| Control | 1 | 1 | 1 | 1 | 1 | 1 | 1 |
| S. aureus + THP1 | 0.576 | 0.412 | 0.05 | 0.129 | 0.047 | 0.201 | 2.446 |

2. Evaluation of Product Biological Efficacy

Protection of the Stem Cell Stock

Topical application of product P1 protected, in a manner clearly superior to product P5, the stem cell markers against the inhibition induced in the model (Table 14).

TABLE 14

Gene expression level of stem cell markers in the model of "immunocompetent" epidermises colonized by S. aureus - Product effect
(T2, Late phase, 16 + 24 h post-colonization)

|  | Control | S. aureus + THP1 | P1 | P5 |
|---|---|---|---|---|
| KRT19 | 1 | 0.412 | 3.14356 | 0.615528 |
| ITGA6 | 1 | 0.05 | 0.18585 | 0.43795 |
| ITGB1 | 1 | 0.129 | 0.57663 | 0.651063 |
| Marker pool average | 1.00 | 0.20 | 1.30 | 0.57 |

Modulation of a Pruritus Marker

The two products tested (P1 and P5) comparably inhibited the expression level of kallikrein 5 to restore a level comparable to the control (Table 15).

Both products modulate the induction of this early marker, involved in pruritus, and which contributes to the development of atopic dermatitis.

TABLE 15

Gene expression level of kallikrein 5 in the model of "immunocompetent" epidermises colonized by S. aureus - Product effect
(T1, Early phase, 16 h post-colonization)

|  | Control | S. aureus + THP1 | P1 | P5 |
|---|---|---|---|---|
| KLK5 | 1.00 | 1.43 | 1.05 | 0.92 |

Restoration of an Immune Defence Marker

The two products tested, P1 and P5, induced a stimulation of TLR2, a receptor involved in the immune response and whose expression is impaired in atopic dermatitis (Table 16).

Product P1 induced a greater increase in TLR2, compared with product P5, in favour of a greater efficacy in protecting mechanisms related to innate immune defences.

TABLE 16

Gene expression level of TLR2 in the model of "immunocompetent" epidermises colonized by S. aureus - Product effect

|  | Control | S. aureus + THP1 | P1 | P5 |
|---|---|---|---|---|
| T1 (16 h) | 1.00 | 0.31 | 0.64 | 0.44 |
| T2 (16 h + 24 h) | 1.00 | 0.20 | 3.04 | 0.71 |

Modulation of TH2 inflammation

In the early phase of the model (T1), both products P1 and P5 similarly inhibited the TSLP expression induced by the model (Table 17).

In the late phase, modelling established atopic dermatitis (T2), only product P1 inhibited TSLP gene expression.

Thus, via its TSLP inhibitory action, product P1 could modulate the induction of TH2 inflammation.

TABLE 17

Gene expression level of TSLP in the model of "immunocompetent" epidermises colonized by S. aureus - Product effect

|  | Control | S. aureus + THP1 | P1 | P2 |
|---|---|---|---|---|
| T1 (16 h) | 1.00 | 1.30 | 0.92 | 1.04 |
| T2 (16 h + 24 h) | 1.00 | 2.45 | 1.35 | 2.89 |

C. Conclusion

This unique model, using reconstructed epidermises from a 1-year-old infant in co-culture with immunocompetent cells, reproduces the role of S. aureus in atopic dermatitis pathophysiology.

The use of this model makes it possible to comparatively evaluate the biological activity of topical products on the protection of stem cells, the barrier and immune defences, as well as on the modulation of pruritus and TH2 inflammation.

IV. Model for Studying S. aureus Biofilm

The biological efficacy of products P1, P5 and P8 against S. aureus biofilm was evaluated in a model of reconstructed epidermises colonized by S. aureus and on which biofilm formation was visualized by electron microscopy.

The biological efficacy of products P1, P5 or P8 against S. aureus biofilm was evaluated in a model of reconstructed epidermises colonized by S. aureus and on which biofilm formation was visualized by electron microscopy.

A. Materials and Methods

The test products (P1, P5 or P8) or 5% xylitol (positive control for inhibition of biofilm formation) were applied topically to reconstructed epidermises at a rate of 30 μL/epidermis, after undergoing slight surface abrasion.

After incubation overnight, the products were removed by rinsing and a $2 \cdot 10^6$ cfu inoculum of *Staphylococcus aureus* (methicillin-resistant *S. aureus*, MRSA; ATCC 33591) was applied to the surface of the reconstructed epidermises.

Biofilm formation and the effect of the product thereon were observed visually by scanning electron microscopy (SEM) 6 and 24 hours after colonization.

B. Results

As of 6 hours after colonization by *S. aureus*, planktonic bacteria cover the surface of the epidermises (FIG. 1A) and produce a polysaccharide matrix characteristic of the initiation of biofilm formation (FIG. 1B).

The application of product P8 exerts an *S. aureus* anti-adhesion effect, visualized by the reduced number of bacteria present on the surface of the epidermises (FIG. 1C).

After 24 hours of colonization (FIGS. 2 and 3), the bacteria are observed in numbers on the surface of the epidermises.

Under the control conditions (untreated epidermises), a dense biofilm is seen (arrows; FIGS. 2A and 2B).

In the control epidermises treated with xylitol, the bacteria appear well individualized. Under these conditions, the bacteria did not produce biofilm; this result validates the test (FIG. 3).

In the presence of products P1 (FIG. 3) and P8 (FIGS. 2C and 2D), well individualized bacteria (cocci) are observed on the surface of the epidermises and are not enveloped in an exopolymeric matrix as in the untreated control conditions. These observations suggest that the topical application of products P1 and P8 inhibited the formation of *S. aureus* biofilm. And, particularly for product P8, an *S. aureus* anti-adhesion effect is observed (FIGS. 1C, 2C, 2D).

P5, in turn, appears to induce partial inhibition of biofilm formation. Indeed, several areas where the bacteria appear well individualized (absence of biofilm) are observed on the surface of the epidermises, while most of the epidermal surface has bacteria covered with biofilm.

C. Conclusion

This model allows electron microscopy monitoring of the kinetics of *S. aureus* biofilm formation on the surface of epidermises and comparative evaluation of the efficacy of topical products in limiting this biofilm, a factor of bacterial virulence and pathogenesis.

Via this model it is possible to classify products according to their efficacy in inhibiting *S. aureus* biofilm: total inhibition, with anti-adhesion effect (e.g. products P1, P8), or partial inhibition (e.g. product P5).

The invention claimed is:

1. A method for evaluating the in vitro efficacy of a cosmetic active agent, an emollient or a formulation in reducing or treating the effects of atopic dermatitis affecting children's skin, said method comprising determining the efficacy of said cosmetic active agent, emollient or formulation in each of the four tests A, B, C and D, wherein:

test A comprises the following steps:
a) obtaining a reconstructed skin model from a skin sample from a child;
b) contacting said cosmetic active agent, emollient or formulation with the reconstructed skin model;
c) contacting the reconstructed skin model with a solution comprising poly(deoxyinosinic-deoxycytidylic) acid and interleukin 1 alpha (IL1α);
d) measuring the expression level of at least one biological marker in the skin; and
e) evaluating the efficacy of said cosmetic active agent, emollient or formulation based on the expression level of the at least one biological marker measured in step d);

test B comprises the following steps:
a) obtaining a reconstructed skin model from a skin sample from a child;
b) contacting said cosmetic active agent, emollient or formulation with the reconstructed skin model;
c) contacting the reconstructed skin model with a solution comprising at least two Th2 cytokines;
d) measuring the expression level of at least one biological marker in the skin model; and
e) evaluating the efficacy of said cosmetic active agent, emollient or formulation based on the expression level of the at least one biological marker measured in step d);

test C comprises the following steps:
a) obtaining a reconstructed skin model from a skin sample from a child;
b) growing the reconstructed skin model in the presence of THP-1 monocytes;
c) contacting said cosmetic active agent, emollient or formulation with the reconstructed skin model;
d) inducing an impairment of the barrier function in the reconstructed skin model;
e) contacting the reconstructed skin model with at least one pathogenic bacterium;
f) measuring the expression and/or activation level of at least one biological marker in the skin model; and
g) evaluating the efficacy of said cosmetic active agent, emollient or formulation based on the expression and/or activation level of the at least one biological marker measured in step f); and test D comprises the following steps:
a) obtaining a reconstructed skin model from a skin sample from a child;
b) contacting said cosmetic active agent, emollient or formulation with the reconstructed skin model;
c) inducing an impairment of the barrier function in the reconstructed skin model;
d) contacting the reconstructed skin model with at least one pathogenic bacterium;
e) measuring the expression and/or activation level of at least one biological marker in the skin model; and
f) evaluating the efficacy of said cosmetic active agent, emollient or formulation based on the expression and/or activation level of the least one biological marker measured in step e).

2. A method for evaluating the tolerance of a cosmetic active agent, an emollient or a formulation by children's atopic skin, said method comprising determining the tolerance of said cosmetic active agent, emollient or formulation by said children's atopic skin in each of the four tests A, B, C and D, wherein:

test A comprises the following steps:
a) obtaining a reconstructed skin model from a skin sample from a child;
b) contacting said cosmetic active agent, emollient or formulation with the reconstructed skin model;

c) contacting the reconstructed skin model with a solution comprising poly(deoxyinosinic-deoxycytidylic) acid and interleukin 1 alpha (IL1α);
d) measuring the expression level of at least one biological marker in the skin model; and
e) determining whether said cosmetic active agent, emollient or formulation is well tolerated by children's atopic skin based on the expression level of the least one biological marker measured step d);

test B comprises the following steps:
a) obtaining a reconstructed skin model from a skin sample from a child;
b) bringing said cosmetic active agent, emollient or formulation into contact with the reconstructed skin model;
c) bringing the reconstructed skin model into contact with a solution comprising at least two Th2 cytokines;
d) measuring the expression level of at least one biological marker in the skin model; and
e) determining whether said cosmetic active agent, emollient or formulation is well tolerated by children's atopic skin based on the expression level of the least one biological marker measured step d);

test C comprises the following steps:
a) obtaining a reconstructed skin model from a skin sample from a child;
b) growing the reconstructed skin model in the presence of THP-1 monocytes;
c) contacting said cosmetic active agent, emollient or formulation with the reconstructed skin model;
d) inducing an impairment of the barrier function in the reconstructed skin model;
e) contacting the reconstructed skin model with at least one pathogenic bacterium;
f) measuring the expression and/or activation level of at least one biological marker in the skin model; and
g) determining whether said cosmetic active agent, emollient or formulation is well tolerated by children's atopic skin based on the expression and/or activation level of the least one biological marker measured step f); and test D comprises the following steps:
a) obtaining a reconstructed skin model from a skin sample from a child;
b) contacting said cosmetic active agent, emollient or formulation with the reconstructed skin model;
c) inducing an impairment of the barrier function in the reconstructed skin model;
d) contacting the reconstructed skin model with at least one pathogenic bacterium;
e) measuring the expression and/or activation level of at least one biological marker in the skin model; and
f) determining whether said cosmetic active agent, emollient or formulation is well tolerated by children's atopic skin based on the expression and/or activation level of the least one biological marker measured step e).

3. A method for identifying a cosmetic active agent, an emollient or a formulation for reducing the effects of atopic dermatitis affecting children's skin, said method comprising determining the efficacy of said cosmetic active agent, emollient or formulation in reducing the effects of atopic dermatitis of children's skin in each of the four tests A, B, C and D, wherein:

test A comprises the following steps:
a) obtaining a reconstructed skin model from a skin sample from a child;
b) contacting the reconstructed skin model with a solution comprising poly(deoxyinosinic-deoxycytidylic) acid and interleukin 1 alpha (IL1α);
c) contacting said cosmetic active agent, emollient or formulation with the reconstructed skin model;
d) measuring the expression level of at least one biological marker in the skin model; and
e) determining whether said candidate cosmetic active agent, emollient or formulation is a cosmetic active agent, emollient or formulation for reducing the effects of atopic dermatitis on children's skin based on the expression level of the least one biological marker measured step d);

test B comprises the following steps:
a) obtaining a reconstructed skin model from a skin sample from a child;
b) contacting the reconstructed skin model with a solution comprising at least two Th2 cytokines;
c) contacting said cosmetic active agent, emollient or formulation with the reconstructed skin model;
d) measuring the expression level of at least one biological marker in the skin model; and
e) determining whether said candidate cosmetic active agent, emollient or formulation is a cosmetic active agent, emollient or formulation for reducing the effects of atopic dermatitis on children's skin based on the expression level of the least one biological marker measured step d);

test C comprises the following steps:
a) obtaining a reconstructed skin model from a skin sample from a child;
b) growing the reconstructed skin model in the presence of THP-1 monocytes;
c) inducing an impairment of the barrier function in the reconstructed skin model;
d) contacting the reconstructed skin model with at least one pathogenic bacterium;
e) contacting said cosmetic active agent, emollient or formulation with the reconstructed skin model;
f) measuring the expression and/or activation level of at least one biological marker in the skin model; and
g) determining whether said candidate cosmetic active agent, emollient or formulation is a cosmetic active agent, emollient or formulation for reducing the effects of atopic dermatitis on children's skin based on the expression and/or activation level of the least one biological marker measured step f); and test D comprises the following steps:
a) obtaining a reconstructed skin model from a skin sample from a child;
b) inducing an impairment of the barrier function in the reconstructed skin model;
c) contacting the reconstructed skin model with at least one pathogenic bacterium;
d) contacting said cosmetic active agent, emollient or formulation with the reconstructed skin model;
e) measuring the expression and/or activation level of at least one biological marker in the skin model; and
f) determining whether said candidate cosmetic active agent, emollient or formulation is a cosmetic active agent, emollient or formulation for reducing the effects of atopic dermatitis on children's skin based on the expression and/or activation level of the least one biological marker measured step e).

4. The method according to claim 1, wherein the at least two Th2 cytokines are selected from the group consisting of IL-4, IL-5, IL-10, IL-13, IL-22, IL-31, TSLP1 and TNFα.

5. The method according to claim 1, wherein the pathogenic bacterium is *Staphylococcus aureus*.

6. The method according to claim 1, wherein said marker is selected from markers of activities that inhibit bacterial physiology, markers of immunity, markers of inflammation, markers of the barrier function and markers preferentially expressed in stem cells.

7. The method according to claim 1, wherein step d) of tests A and B, step f) of test C, and step e) of test D comprise measuring a combination of biological markers, said combination comprising at least two markers, said markers being selected from at least two different categories of markers selected from markers of activities that inhibit bacterial physiology, markers of immunity, markers of inflammation, markers of the barrier function and markers preferentially expressed in stem cells.

8. The method according to claim 6, wherein the bacterial physiology-inhibiting activity is selected from inhibition of bacterial proliferation and inhibition of biofilm formation.

9. The method according to claim 6, wherein:
the marker of immunity is HBD2 or TLR2,
the marker of inflammation is CCL2, CXCL1, CCL7, IL6, IL18, CCL3, CCL5, CCL7, KLK5 or TSLP,
the marker of barrier function is FLG, KRT1, KRT10, SCEL, BARX2, LOR, IVL, TGM1, DSG1, CDSN, CLDN1, CASP14, SMPD1, GBA, LASS6, NMF or the ceramides, or
the marker preferentially expressed in stem cells is KRT15, KRT19, NOTCH1, BIRC5, ITGA6, ITGB1 or ITGB4.

10. The method according to claim 1, wherein the skin sample comes from a donor selected from the group consisting of newborns aged between 0 and 1 month, infants aged between 1 month and 2 years, and children aged between 2 years and 16 years.

11. The method according to claim 1, wherein the skin sample comes from skin with a phototype I, II, III, IV, V or VI.

12. The method according to claim 1, wherein the reconstructed skin model is selected from suspended skin cell cultures, monolayer skin cell cultures, bilayer skin cell cultures, reconstructed skin cultures and reconstructed mucosal cultures.

13. The method according to claim 12, wherein the cells of said model come from a skin tissue explant or from stem cells differentiated into skin cells.

14. The method according to that claim 1, wherein said model comprises at least fibroblasts or keratinocytes.

15. The method according to claim 2, wherein the at least two Th2 cytokines are selected from the group consisting of IL-4, IL-5, IL-10, IL-13, IL-22, IL-31, TSLP1 and TNFα.

16. The method according to claim 2, wherein the pathogenic bacterium is *Staphylococcus aureus*.

17. The method according to claim 3, wherein the at least two Th2 cytokines are selected from the group consisting of IL-4, IL-5, IL-10, IL-13, IL-22, IL-31, TSLP1 and TNFα.

18. The method according to claim 3, wherein the pathogenic bacterium is *Staphylococcus aureus*.

19. The method according to claim 2, wherein the biological marker is selected from markers of immunity, markers of inflammation, markers of barrier function, and markers preferentially expressed in stem cells.

20. The method according to claim 19, wherein:
the marker of immunity is HBD2 or TLR2,
the marker of inflammation is CCL2, CXCL1, CCL7, IL6, IL18, CCL3, CCL5, CCL7, KLK5 or TSLP,
the marker of barrier function is FLG, KRT1, KRT10, SCEL, BARX2, LOR, IVL, TGM1, DSG1, CDSN, CLDN1, CASP14, SMPD1, GBA, LASS6, NMF or the ceramides, or
the marker preferentially expressed in stem cells is KRT15, KRT19, NOTCH1, BIRC5, ITGA6, ITGB1 or ITGB4.

21. The method according to claim 3, wherein the biological marker is selected from markers of immunity, markers of inflammation, markers of barrier function, and markers preferentially expressed in stem cells.

22. The method according to claim 21, wherein:
the marker of immunity is HBD2 or TLR2,
the marker of inflammation is CCL2, CXCL1, CCL7, IL6, IL18, CCL3, CCL5, CCL7, KLK5 or TSLP,
the marker of barrier function is FLG, KRT1, KRT10, SCEL, BARX2, LOR, IVL, TGM1, DSG1, CDSN, CLDN1, CASP14, SMPD1, GBA, LASS6, NMF or the ceramides, or
the marker preferentially expressed in stem cells is KRT15, KRT19, NOTCH1, BIRC5, ITGA6, ITGB1 or ITGB4.

* * * * *